United States Patent
Shimuta et al.

(10) Patent No.: US 8,332,019 B2
(45) Date of Patent: Dec. 11, 2012

(54) ELECTROCARDIOGRAPHIC SIGNAL DETECTION DEVICE

(75) Inventors: Toru Shimuta, Kyoto-Fu (JP); Eiji Takahashi, Kyoto-Fu (JP)

(73) Assignee: Murata Manufacturing Co., Ltd., Nagaokakyo-Shi, Kyoto-fu (JP)

( * ) Notice: Subject to any disclaimer, the term of this patent is extended or adjusted under 35 U.S.C. 154(b) by 0 days.

(21) Appl. No.: 13/248,109

(22) Filed: Sep. 29, 2011

(65) Prior Publication Data

US 2012/0022385 A1 Jan. 26, 2012

Related U.S. Application Data

(63) Continuation of application No. PCT/JP2009/070333, filed on Dec. 3, 2009.

(30) Foreign Application Priority Data

Apr. 2, 2009 (JP) ................................. 2009-090203
Sep. 15, 2009 (JP) ................................. 2009-213372

(51) Int. Cl.
   *A61B 5/04* (2006.01)
(52) U.S. Cl. ...................................... 600/509
(58) Field of Classification Search .................... 600/509
   See application file for complete search history.

(56) References Cited

U.S. PATENT DOCUMENTS

| | | | |
|---|---|---|---|
| 3,882,846 A | 5/1975 | Fletcher et al. | |
| 5,230,680 A | 7/1993 | Wu | |
| 5,749,367 A | 5/1998 | Gamlyn et al. | |
| 7,622,736 B2 * | 11/2009 | Moriya et al. | 257/48 |
| 7,663,607 B2 | 2/2010 | Hotelling et al. | |
| 2005/0004482 A1 | 1/2005 | Drakulic | |

FOREIGN PATENT DOCUMENTS

| | | |
|---|---|---|
| JP | 11-104252 A | 4/1999 |
| JP | 11-512012 T | 10/1999 |
| JP | 11-299740 A | 11/1999 |
| JP | 2003-144403 A | 5/2003 |
| JP | 2005-046215 A | 2/2005 |
| JP | 2007-527261 A | 9/2007 |
| JP | 2007-533044 A | 11/2007 |

OTHER PUBLICATIONS

PCT/JP2009/070333 Written Opinion dated Sep. 2, 2010.

* cited by examiner

*Primary Examiner* — George Manuel
(74) *Attorney, Agent, or Firm* — Dickstein Shapiro LLP

(57) ABSTRACT

An electrocardiographic signal detection device that includes at least one pair of electrodes that detect electrical signals of a living body; an insulating film disposed on the at least one pair of electrodes, the insulating film having a living body contact surface; a differential amplifier that generates an electrocardiographic signal by differentially amplifying the electrical signals of the living body; and an arithmetic processing unit that obtains biological information based on the electrocardiographic signal generated by the differential amplifier, wherein the insulating film and the at least one pair of electrodes are arranged such that the electrical signals of the living body are detected through capacitive coupling between the living body in contact with the living body contact surface of the insulating film and the at least one pair of electrodes.

19 Claims, 16 Drawing Sheets

ELECTROCARDIOGRAPHIC SIGNAL DETECTION DEVICE

CROSS REFERENCE TO RELATED APPLICATIONS

The present application is a continuation of International application No. PCT/JP2009/070333, filed Dec. 3, 2009, and which claims priority to Japanese Patent application No. 2009-090203, filed Apr. 2, 2009, and Japanese Patent application No. 2009-213372, filed Sep. 15, 2009, the entire contents of each of these references being incorporated herein by reference in their entirety.

FIELD OF THE INVENTION

The present invention relates to an electrocardiographic signal detection device for detecting an electrocardiographic signal from a living body.

BACKGROUND OF THE INVENTION

There is known an electrocardiographic signal detection device for extracting the activity of a human heart as an electrocardiographic signal, and acquiring biological information, such as electrocardiographic data, based on the electrocardiographic signal for the purpose of diagnosis, treatment, etc. of heart diseases.

That type of electrocardiographic signal detection device is classified into a large-scaled device that is used by doctors in medial institutions, e.g., hospitals, and a portable device that is used by ordinary persons in homes.

The large-scaled electrocardiographic signal detection device includes, for example, a desktop computer having a sophisticated processing function to analyze the electrocardiographic data, a plurality of, e.g., twelve, electrodes connected to the computer through respective cables, a desktop display device for monitoring electrocardiographic waveforms, etc., and a printer for printing out the electrocardiographic waveforms, etc. A doctor, for example, attaches the electrodes to the legs and arms of a subject (examinee) lying on a bed, and operates the computer. Responsively, the electrocardiographic signal detection device detects the electrocardiographic signal of the subject and precisely performs an analysis of the electrocardiographic data, etc., thereby generating professional information that is directly useful for, e.g., diagnosis and treatment of arrhythmia (irregular pulse), angina pectoris (stricture of the heart), etc.

On the other hand, the portable electrocardiographic signal detection device includes a small-sized housing capable of being lifted up by one hand. An IC chip, a memory, etc., which have the function of performing a simplified analysis of the electrocardiographic data, are contained in the housing. Several, e.g., two or three, electrodes, a small-sized liquid crystal display panel, an operating button, etc. are arranged on an outer surface of the housing. A user puts the fingers or the palms of the hands on the electrodes of the electrocardiographic signal detection device and then operates the operating button. Responsively, the electrocardiographic signal detection device detects an electrocardiographic signal of the user and generates electrocardiographic data, etc. Although the electrocardiographic data generated by the small-sized electrocardiographic signal detection device is simpler than that generated by the large-sized electrocardiographic signal detection device described above, the former data is also useful as, e.g., information for notifying a doctor of symptoms of heart diseases, such as palpitation (see Patent Documents 1 to 3).

Patent Document 1: Japanese Unexamined Patent Application Publication No. 11-299740
Patent Document 2: Japanese Unexamined Patent Application Publication No. 2003-144403
Patent Document 3: Japanese Unexamined Patent Application Publication No. 2005-46215

The electrodes employed in the above-described electrocardiographic signal detection device of the related art are each made of, e.g., metal including silver-silver chloride. When the electrocardiographic signal is detected, the electrodes are brought into direct contact with the human skin. After the detection of the electrocardiographic signal, the electrodes may be left to stand for a long time in some cases while the electrodes are exposed to open air in a state that moisture, etc. attributable to the contact with the human skin are kept adhering to the electrodes.

Therefore, if the electrocardiographic signal detection device is held in a poor management situation, there is a risk that durability may be reduced due to deterioration of the electrodes. Also, there is a risk that when an electrocardiogram is measured using the deteriorated electrodes, accuracy of the measurement may be degraded.

In the above-described portable electrocardiographic signal detection device of the related art, the plurality of electrodes need to be arranged on an outer surface of the housing such that the user can easily make contact, e.g., the fingers or the palms contact with the electrodes. Thus, a space sufficient to arrange the electrodes in a desired layout has to be secured on the outer surface of the housing. For that reason, it is difficult to realize a further reduction in size of the electrocardiographic signal detection device.

SUMMARY OF THE INVENTION

The present invention has been accomplished in view of the above-described problems, etc., and an object of the present invention is to provide an electrocardiographic signal detection device, which can improve durability and which can reduce a device size.

To achieve the above object, the present invention provides an electrocardiographic signal detection device comprising at least one pair of electrodes for detecting electrical signals of a living body, an insulating film disposed on the at least one pair of electrodes, the insulating film has a contact surface which is a surface opposite to a surface being in contact with the at least one pair of electrodes and the contact surface is to be contacted with the living body, a differential amplifier for generating an electrocardiographic signal by differentially amplifying the electrical signals of the living body, which are detected through capacitive coupling between the living body contacted with the contact surface of the insulating film and the at least one pair of electrodes, and an arithmetic processing unit for obtaining biological information based on the electrocardiographic signal generated by the differential amplifier.

According to the present invention described above, since the insulating film is disposed on the electrodes and the electrical signals relating to the electrocardiographic signal are detected through capacitive coupling between the electrodes and the living body, the electrodes and the living body are avoided from directly contacting with each other, and the electrodes are not exposed to open air. As a result, moisture, etc. can be prevented from adhering to the electrodes, and deterioration of the electrodes can be suppressed. It is hence possible to enhance durability of the electrocardiographic signal detection device and to prolong the service life thereof.

Also, the present invention provides an electrocardiographic signal detection device comprising a housing, a display window provided in the housing, at least one pair of electrodes disposed on a surface of the display window, made of a transparent electroconductive material, and detecting electrical signals of a living body, an insulating film disposed on the at least one pair of electrodes, made of a transparent insulating material, the insulating film has a contact surface which is a surface opposite to a surface being in contact with the at least one pair of electrodes and the contact surface is to be contacted with the living body, a differential amplifier for generating an electrocardiographic signal by differentially amplifying the electrical signals of the living body, which are detected through capacitive coupling between the living body contacted with the contact surface of the insulating film and the at least one pair of electrodes, an arithmetic processing unit for obtaining biological information based on the electrocardiographic signal generated by the differential amplifier, a display panel disposed in the housing and displaying display information through the display window, the at least one pair of electrodes, and through the insulating film, and an information display circuit for displaying the display information on the display panel.

According to the present invention described above, since the transparent electrodes are formed on the surface of the display window and the transparent insulating film is formed on the electrodes, the electrodes having good durability can be arranged in overlapped relation to a display area of the display panel without impeding the display information on the display panel. As a result, a size reduction and a longer service life of the electrocardiographic signal detection device can be realized at the same time.

Also, the display information indicating a manner of measuring an electrocardiogram, a posture in the measurement, etc. can be displayed in overlapped or adjacent relation to the electrodes in a screen of the display panel. Therefore, operability of the electrocardiographic signal detection device can be improved, thus enabling even an ordinary person to easily perform electrocardiographic measurement.

Further, operating buttons utilizing a touch panel, a photosensor for photo-plethysmography, etc. can be arranged below the electrodes. Accordingly, an electrocardiographic signal detection device having a smaller size and a more sophisticated function can be realized.

Moreover, the present invention provides the electrocardiographic signal detection device further comprising a touch panel disposed at an underside of the display window and adapted for entering input information through the display window, a drive circuit for driving the touch panel, and a control unit for controlling the arithmetic processing unit in accordance with the input information entered through the touch panel.

According to the present invention described above, the following advantageous effect can be obtained in addition to the above-described advantages. Since the contact between the living body and the insulating film disposed on the electrode is detected with the touch panel, the operability of the electrocardiographic signal detection device can be improved. Thus, a function convenient for a general user can be realized, for example, in point of automatically starting the detection of the electrical signals relating to the electrocardiographic signal at the same time as when user's fingers are brought into contact with the insulating film disposed on the electrodes.

Still further, the present invention provides an electrocardiographic signal detection device comprising a housing, a display window provided in the housing, an operating button disposed on the housing, a first electrode disposed on the operating button, made of an electroconductive material, and detecting an electrical signal of a living body, a first insulating film disposed on the first electrode, at least one second electrode disposed on a surface of the display window, made of a transparent electroconductive material, and detecting an electrical signal of the living body, a second insulating film disposed on the at least one second electrode, made of a transparent insulating material, and having one surface, which is positioned oppositely away from the other surface being in contact with the at least one second electrode and which serves as a contact surface to be contacted with the living body, a differential amplifier for generating an electrocardiographic signal by differentially amplifying one electrical signal of the living body, which is detected through capacitive coupling between one part of the living body contacted with the contact surface of the second insulating film and the at least one second electrode, and the other electrical signal of the living body, which is detected through capacitive coupling between another part of the living body contacted with the contact surface of the first insulating film and the first electrode, an arithmetic processing unit for obtaining biological information based on the electrocardiographic signal generated by the differential amplifier, a display panel disposed in the housing and displaying display information through the display window, the at least one second electrode, and through the second insulating film, and an information display circuit for displaying the display information on the display panel.

According to the present invention described above, since not only the contact between the living body and the insulating film disposed on the electrode, but also the operation of the operating button can be detected at the same time, the operability of the electrocardiographic signal detection device can be improved. Thus, a function convenient for a general user can be realized, for example, in point of automatically starting the detection of the electrical signals relating to the electrocardiographic signal when the user presses the operating button while keeping the finger in a state contacted with the insulating film disposed on the electrode.

Also, the above-described electrocardiographic signal detection device according to the present invention further comprises a touch panel disposed at an underside of the display window and adapted for entering input information through the display window, a drive circuit for driving the touch panel, and a control unit for controlling the arithmetic processing unit in accordance with the input information entered through the touch panel.

According to the present invention described above, since the contact between the living body and the insulating film disposed on the electrode is detected with the touch panel, the operability of the electrocardiographic signal detection device can be improved in addition to the above-described advantageous effects.

In the electrocardiographic signal detection device according to the present invention, the at least one pair of electrodes are connected to input terminals of the differential amplifier for differentially amplifying the electrical signals of the living body, which are detected through capacitive coupling between the living body and the at least one pair of electrodes, at least one clamp circuit including at least one high-impedance element is connected to the input terminal of the differential amplifier, a potential at a connected end of the clamp circuit is fixedly held constant, and an impedance when looking at the differential amplifier from the connected end of the clamp circuit is set to be larger than an impedance of the clamp circuit.

In trying to detect the biological signal through the capacitive coupling between the electrode and the living body, if an input impedance when looking at the differential amplifier from the electrode is low, a loss in a frequency band of the electrical signal of the living body is increased and the electrical signal cannot be detected.

In contrast, according to the present invention described above, since the clamp circuit is constituted by using the high-impedance element and the impedance when looking at an input terminal of the differential amplifier from the connected end of the clamp circuit is set to be larger than the impedance of the clamp circuit, the loss in the frequency band of the electrical signal of the living body can be reduced. Further, since a reference potential at, e.g., the input terminal of the differential amplifier or in a stage upstream thereof can be fixedly held, variations in a central potential of the electrical signal of the living body are reduced. As a result, an SN (Signal to Noise) ratio is increased and the electrical signal of the living body can be stably detected.

BRIEF DESCRIPTION OF THE DRAWINGS

in FIG. 12.

in FIG. 19.

Figure 1:
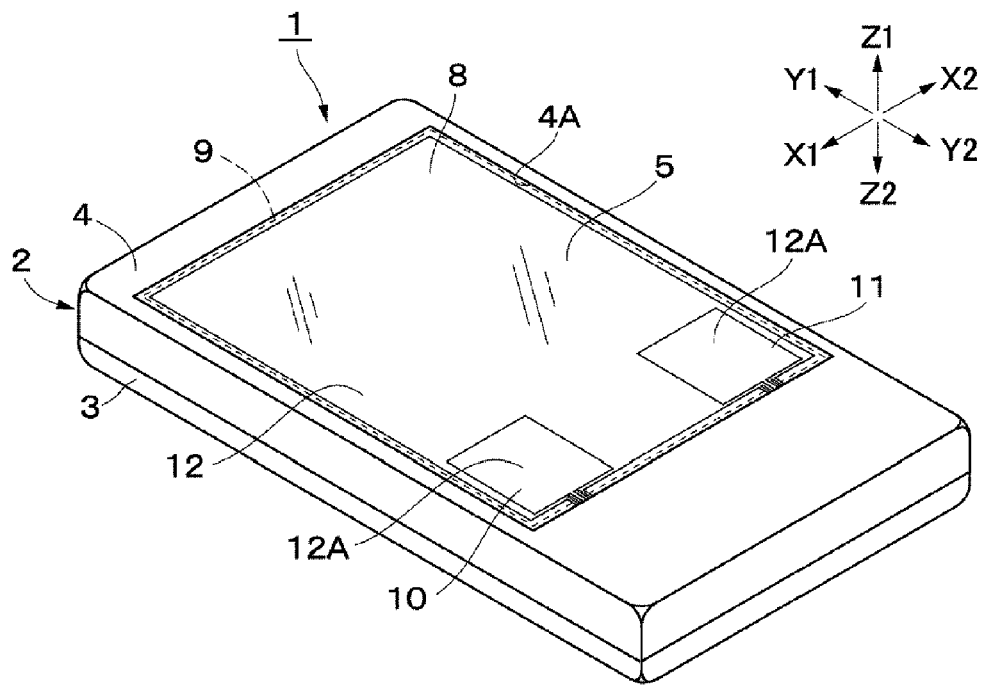
FIG. 1 is a perspective view of an electrocardiographic signal detection device according to a first embodiment of the present invention.

REFERENCE NUMBERS 1, 41, 61, 81, 91, 101 electrocardiographic signal detection device
2, 42, 62, 82 housing
4A, 42A, 62A, 82A opening
5, 43, 63, 83 display window
8, 44, 64, 84 display panel
9 touch panel
10, 11 transparent electrode
12 transparent insulating film
12A contact surface
21 differential amplifier
22 arithmetic processing unit
23 information display circuit
24 touch panel drive circuit
25 control unit
45, 65, 66, 85 operating button
46, 47, 67, 68, 86, 87 electrode
48, 49, 69, 70, 89 insulating film
88 insulated portion
94, 111 clamp circuit
94B, 111B diode (high-impedance element)
105, 121 first clamp circuit
105B, 121B diode (first high-impedance element)
106, 122 second clamp circuit
106B, 122B diode (second high-impedance element)

DETAILED DESCRIPTION OF THE INVENTION

Embodiments of the present invention will be described below with reference to the attached drawings. At the outset, a first embodiment of the present invention is described.

Figure 2:
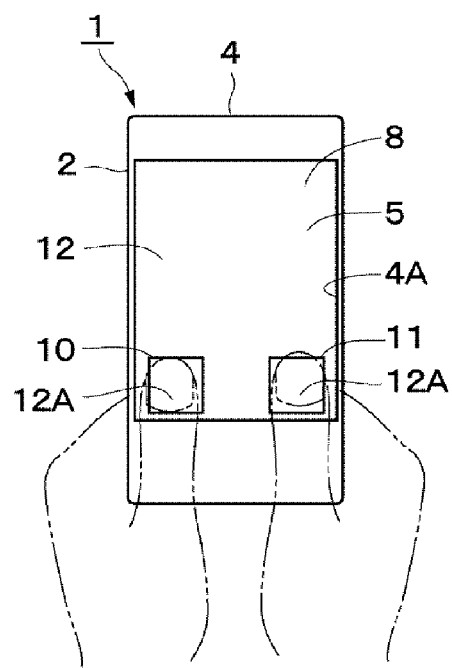
FIG. 2 is an explanatory view of the electrocardiographic signal detection device according to the first embodiment in a state where electrocardiographic measurement is performed.

In FIG. 1, an electrocardiographic signal detection device 1 according to the first embodiment of the present invention is a portable device, which can perform simplified electrocardiographic measurement and which can be readily lifted up by a user with one hand. The electrocardiographic signal detection device 1 is able to detect biological signals, i.e., electrical signals each varying depending on the activity of the heart of a human being (living body), from the thumbs of both the human hands as illustrated in FIG. 2, to generate an electrocardiographic signal based on the biological signals, and to generate biological information, such as electrocardiographic data, based on the electrocardiographic signal.

For the sake of convenience in explanation, the directions indicated by arrows Z1 and Z2 in FIG. 1 are defined respectively as an upward direction and a downward direction. The directions indicated by arrows X1 and X2 in FIG. 1 are defined respectively as a leftward direction and a rightward direction. The directions indicated by arrows Y1 and Y2 in FIG. 1 are defined respectively as a rearward direction and a forward direction.

A housing 2 forms an outer shell of the electrocardiographic signal detection device 1. The housing 2 is made up of a lower case 3 and an upper case 4. The lower case 3 is positioned in a lower portion of the electrocardiographic signal detection device 1, and it contains a base plate 6, a display panel 8, a touch panel 9, connectors 16, a processing circuit unit 18, etc. (each described later). The upper case 4 is positioned above the lower case 3 to cover an upper portion of the electrocardiographic signal detection device 1. The lower case 3 and the upper case 4 are each made of an insulating material, e.g., resin. The upper case 4 includes an opening 4A formed therein for attachment of a display window 5 thereto.

The display window 5 is attached to the opening 4A of the upper case 4. The display window 5 is made of a transparent insulating material, e.g., transparent resin. In more detail, the display window 5 is formed of a transparent resin film of, e.g., polyethylene naphthalate (PEN) or polyethylene terephthalate (PET). Alternatively, the display window 5 may be made of glass. The display window 5 encloses the opening 4A and entirely covers the upper surface side of a liquid crystal display screen of the display panel 8.

Figure 3:
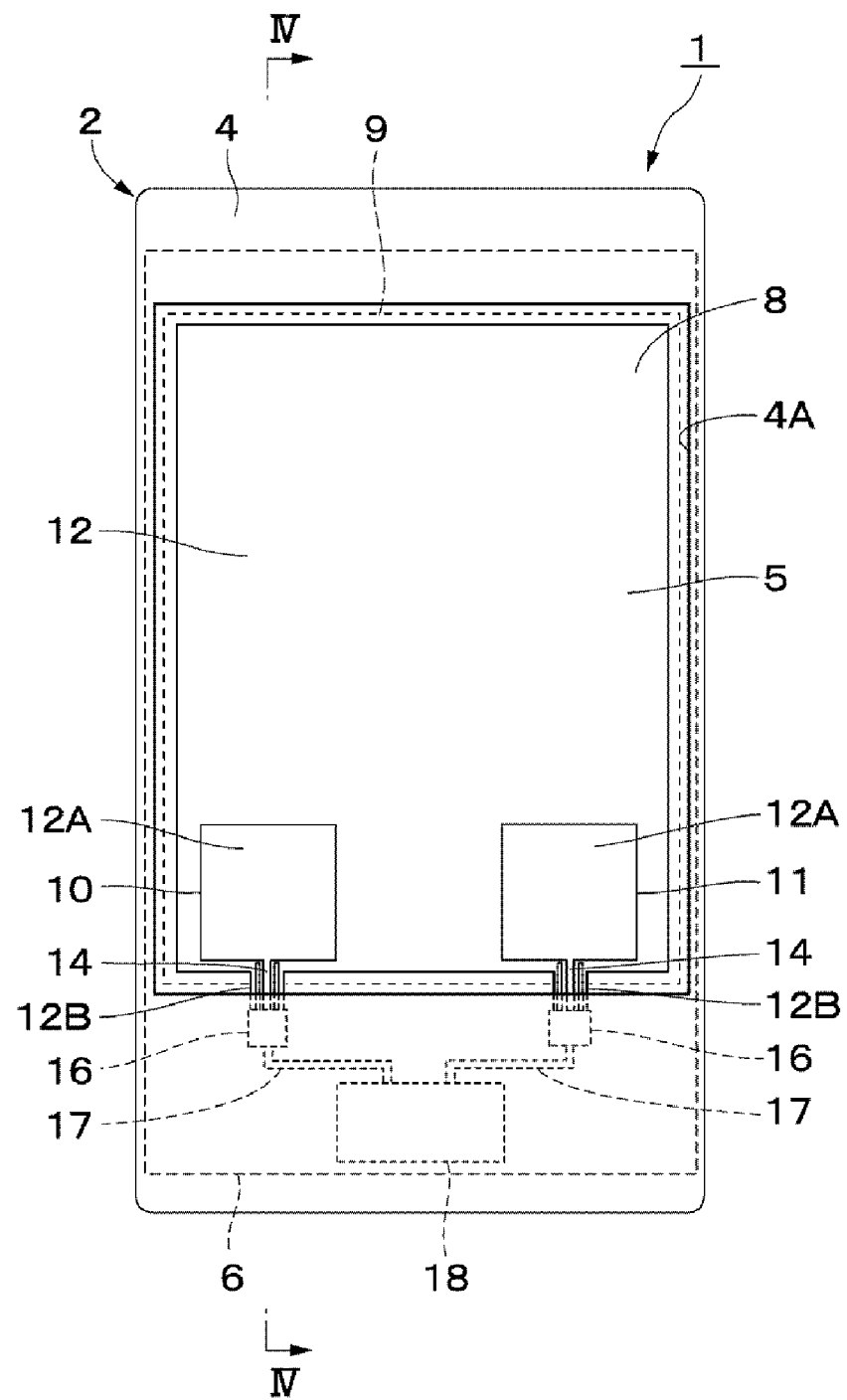
FIG. 3 is a front view of the electrocardiographic signal detection device according to the first embodiment of the present invention.
Figure 4:
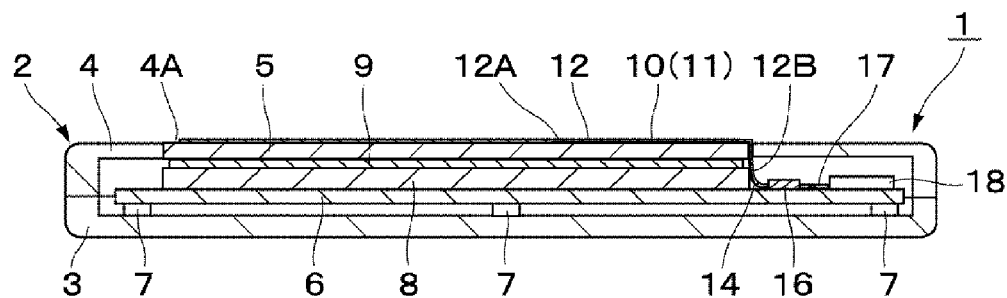
FIG. 4 is a longitudinal sectional view of the electrocardiographic signal detection device taken along a line IV-IV in FIG. 3 in a direction denoted by arrow.

In FIGS. 3 and 4, the base plate 6 is mounted inside the lower case 3 by using support members 7. The display panel 8, the touch panel 9, the connectors 16, the processing circuit unit 18, etc. (each described later) are mounted on the base plate 6.

The display panel 8 is disposed inside the lower case 3 and is positioned below the display window 5. The display panel 8 is, for example, a liquid-crystal display panel unit having a liquid crystal display screen. In more detail, the display panel 8 is mounted on the base plate 6, and a connection terminal (not shown) of the display panel 8 is electrically connected to a display connection terminal (not shown) provided on the base plate 6. The shape, size and position of the liquid crystal display screen disposed on the upper surface of the display panel 8 are set corresponding to the opening 4A of the upper cover 4. The user can view information displayed on the liquid crystal display screen of the display panel 8 while seeing through the display window 5 attached to the opening 4A, the touch panel 9 disposed between the display window 5 and the display panel 8, transparent electrodes 10 and 11 disposed on the display window 5, a transparent adhesive layer 13, and through a transparent insulating film 12.

The touch panel 9 is disposed at the underside of the display window 5 and allows input information to be entered through the display window 5. In more detail, the touch panel 9 is disposed between the display window 5 and the display panel 8, and it covers substantially the entire liquid crystal display screen. The touch panel 9 is, for example, a touch panel of the resistance film type or the electrostatic capacity type. A connection terminal (not shown) of the touch panel 9 is electrically connected to a touch-panel connection terminal (not shown) provided on the base plate 6. When, for example, the human finger is contacted with the transparent insulating film 12 that is formed on an upper surface of the display window 5 and on an upper surface of each of the transparent electrodes 10 and 11, the touch panel 9 outputs a contact detection signal, including information of the contact position, to a control unit 25.

Two transparent electrodes 10 and 11 detect biological signals from the thumbs of both the human hands. The transparent electrodes 10 and 11 are disposed on the upper surface (front surface) of the display window 5. The transparent electrodes 10 and 11 are each made of a transparent electroconductive metal material, e.g., ITO (Indium Tin Oxide), ZnO (Zinc Oxide), $SnO_2$ (Stannic (Tin) Oxide), $TiO_2$ (Titanium Oxide), or a magnesium-base nonoxide. Alternatively, the transparent electrodes 10 and 11 may be each made of a transparent electroconductive resin.

Each of the transparent electrodes 10 and 11 has a size and a shape suitable for detecting the biological signal from a tip portion of the human thumb. For example, it is formed in a square shape with one side having a length of about 1.5 cm. Further, the transparent electrodes 10 and 11 are each a thin film having a thickness of, e.g., several μm to several tens μm, and are each formed in a predetermined pattern on the display window 5 with the transparent adhesive layer 13 interposed therebetween. Alternatively, the transparent electrodes 10 and 11 may have a circular shape with a diameter of about 1.5 cm.

Moreover, as illustrated in FIG. 2, the transparent electrodes 10 and 11 are arranged at such positions that the user can easily make the thumbs of both the hands contacted with portions of the touch panel 9, which correspond to the transparent electrodes 10 and 11, in a state grasping the electrocardiographic signal detection device 1 by both the hands. More specifically, one transparent electrode 10 is arranged at a forward left corner within the upper surface of the display window 5 on the side closer to the user, and the other transparent electrode 11 is arranged at a forward right corner within the upper surface of the display window 5 on the side closer to the user. In addition, the transparent electrodes 10 and 11 are arranged such that, when viewing the electrocardiographic signal detection device 1 from above, the whole of the transparent electrodes 10 and 11 is overlapped with the liquid crystal display screen of the display panel 8 and the touch panel 9.

The transparent insulating film 12 is disposed over the transparent electrodes 10 and 11 as described below. The transparent electrodes 10 and 11 detect the biological signals from the user's thumbs through capacitive coupling between the user's thumbs contacted with two contact surfaces 12A of the transparent insulating film 12 and the transparent electrodes 10, 11.

The transparent insulating film 12 covers an entire upper surface of the display window 5 on which the transparent electrodes 10 and 11 are formed. Stated another way, the transparent insulating film 12 not only directly covers respective upper surfaces of the transparent electrodes 10 and 11, but also covers a remaining portion of the upper surface of the display window 5, in which the transparent electrodes 10 and 11 are not formed, with the adhesive layer 13 interposed therebetween. Further, portions of the upper surface of the transparent insulating film 12 opposing to the transparent electrodes 10 and 11, i.e., partial upper surfaces of the transparent insulating film 12 positioned oppositely away from its partial lower surfaces being in contact with the transparent electrodes 10 and 11, serve as the contact surfaces 12A. When detecting the biological signals, the user brings the thumbs into contact with the contact surfaces 12A.

The transparent insulating film 12 is formed, for example, by coating a transparent insulating material, e.g., polyethylene naphthalate (PEN) or polyethylene terephthalate (PET), over the respective upper surfaces of the transparent electrodes 10 and 11 and the remaining portion of the upper surface of the display window 5, in which the transparent electrodes 10 and 11 are not formed. The thickness of the transparent insulating film 12 is, e.g., several μm to several tens μm.

Figure 5:
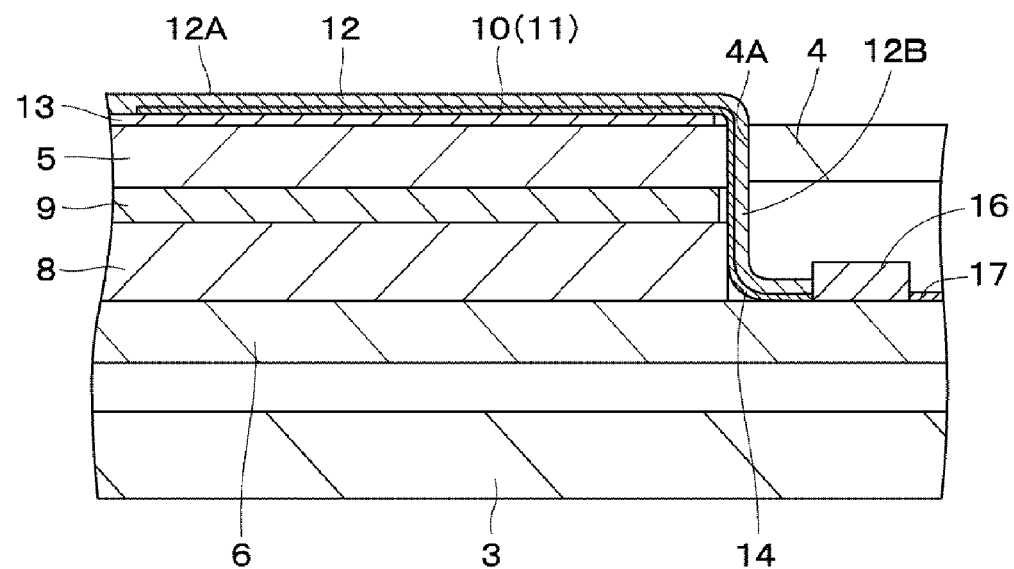
FIG. 5 is a longitudinal sectional view illustrating, in an enlarged scale, a transparent electrode, etc., in the electrocardiographic signal detection device.

Further, as illustrated in FIG. 3, two line protective portions 12B are formed at a forward-side edge of the transparent insulating film 12 to protect current carrying lines 14 and ground lines 15 (each described below). As illustrated in FIG. 5, the line protective portions 12B are each formed by partly extending a forward-side edge portion of the transparent insulating film 12 toward the connector 16 (described later) that is disposed on the base plate 6. The line protective portions 12B cover respective surfaces of the current carrying lines 14 and the ground lines 15 (each described below).

Figure 6:
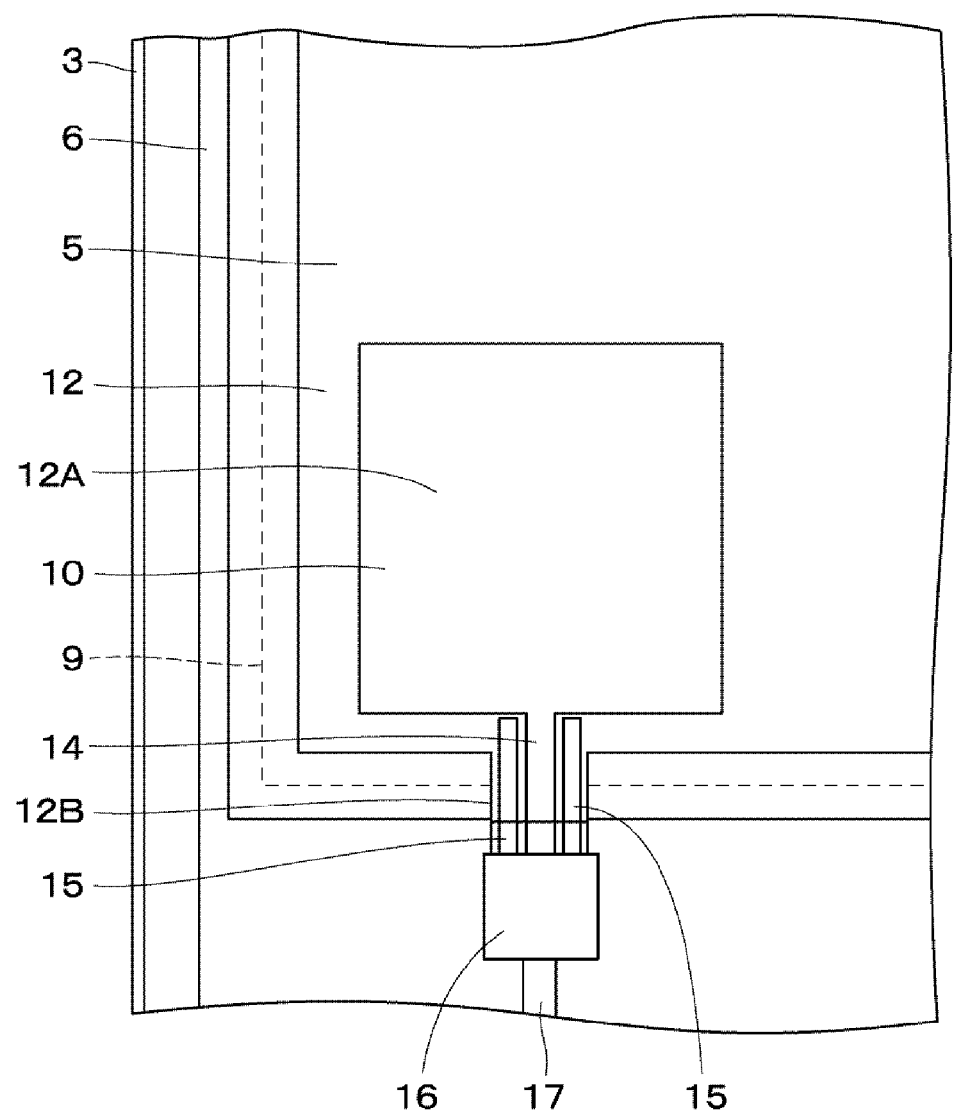
FIG. 6 is an enlarged front view illustrating, in the same direction as that in the case of FIG. 3, the transparent electrode, a connector, etc. on one side of the electrocardiographic signal detection device in a state that an upper case of a housing is removed.

Two current carrying lines 14 electrically connect the transparent electroconductive films 10 and 11 and signal terminals of the corresponding connectors 16. The current carrying lines 14 are each made, for example, of the same transparent electroconductive material as that of the transparent electrodes 10 and 11. Further, as illustrated in FIGS. 5 and 6, the proximal ends of the current carrying lines 14 are connected respectively to the transparent electrodes 10 and 11, while the distal ends of the current carrying lines 14 are extended downward together with the line protective portions 12B into the housing 2 after passing through a gap between a forward-side end surface of the display window 5 and a forward-side edge of the opening 4A in the upper case 4. Further, the distal ends of the current carrying lines 14 are connected to the signal terminals of the corresponding connectors 16.

The ground lines 15 are positioned on both the left and right sides of each current carrying line 14 and are each arranged with a predetermined distance left from the relevant current carrying line 14. The ground lines 15 are each made of an electroconductive material. Further, the ground lines 15 are each extended parallel to the current carrying line 14 from the proximal end side to the distal end side thereof, and the distal end of each ground line 15 is connected to a ground terminal of the connector 16. By surrounding each current carrying line 14 with the two ground lines 15 as described above, radiation noise can be effectively avoided from being superimposed on the biological signal that flows through each current carrying line 14.

Two connectors 16 are disposed on the base plate 6. Each of the connectors 16 not only connects the current carrying line 14 to the processing circuit unit 18 (described later) through a connecting line 17, but also connects the ground lines 15 to a ground portion (not shown) provided on the base plate 6. Thus, each connector 16 includes a signal terminal (not shown) for connecting the current carrying line 14 and the connecting line 17, and a ground terminal (not shown) for connecting the ground lines 15 and the ground portion provided on the base plate 6.

Figure 7:
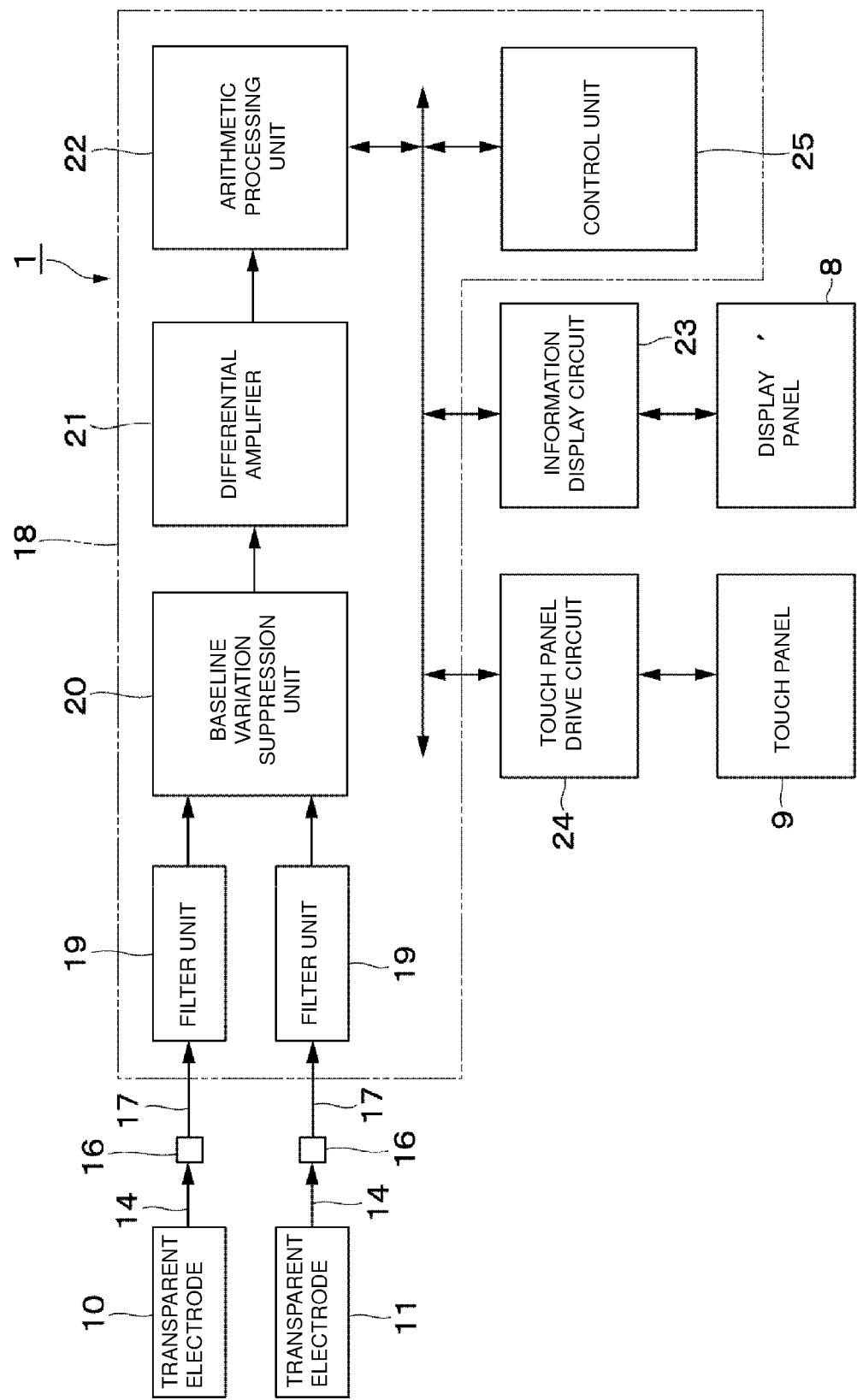
FIG. 7 is a circuit diagram illustrating the electrical configuration of the electrocardiographic signal detection device.

The processing circuit unit 18 is disposed on the base plate 6. As illustrated in FIG. 7, the processing circuit unit 18 includes two filter units 19, a baseline variation suppression unit 20, a differential amplifier 21, an arithmetic processing unit 22, an information display circuit 23, a touch panel drive circuit 24, and a control unit 25.

The filter units 19 are disposed in the input terminal side of the processing circuit unit 18, and they serve to reduce noises in the biological signals detected from the user's thumbs. In more detail, the filter units 19 are connected respectively to the transparent electrodes 10 and 11 through the current carrying lines 14, the signal terminals of the connectors 16, and the connecting lines 17. The filter units 19 reduce noises in the biological signals that are detected through capacitive coupling between the user's thumbs and the transparent electrodes 10, 11 when the user's thumbs are brought into contact with the contact surfaces 12A of the transparent insulating film 12 on the transparent electrodes 10 and 11.

The filter units 19 are each constituted by a low-pass filter. Alternatively, a high-pass filter may be added to the filter unit 19. In order to reduce waveform distortion of the electrocardiographic signal generated by the differential amplifier 21, the input impedance of the filter unit 19 is desirably set relatively high, e.g., 1 GΩ to 10 TΩ.

The baseline variation suppression unit 20 is disposed in a stage downstream of the filter units 19. The baseline variation suppression unit 20 suppresses variations in respective baselines of the biological signals output from the filter units 19.

The differential amplifier 21 differentially amplifies the biological signals output from the baseline variation suppression unit 20, thereby generating the electrocardiographic signal. The differential amplifier 21 is constituted by a differential amplification circuit including, e.g., an operational amplifier, etc. The input impedance of a commonly used operational amplifier is 1 GΩ or more. Therefore, the input impedance of the differential amplifier 21 is 1 GΩ or more. Stated another way, the differential amplifier 21 generates the electrocardiographic signal by differentially amplifying the biological signal, which has been detected from the thumb of the user's left hand by one transparent electrode 10 and which has been input thereto through one filter unit 19 and the baseline variation suppression unit 20, and the biological signal, which has been detected from the thumb of the user's right hand by the other transparent electrode 11 and which has been input thereto through one filter unit 19 and the baseline variation suppression unit 20.

The arithmetic processing unit 22 is disposed in a stage downstream of the differential amplifier 21. The arithmetic processing unit 22 is constituted, along with the control unit 25, by a Central Processing Unit (CPU). The arithmetic processing unit 22 executes computations to obtain biological information, such as electrocardiographic data, based on the electrocardiographic signal generated by the differential amplifier 21.

The information display circuit 23 controls information displayed on the liquid crystal display screen of the display panel 8, and it is electrically connected to the display panel 8. The touch panel drive circuit 24 drives the touch panel 9, and it is electrically connected to the touch panel 9.

The control unit 25 controls the display panel 8, the arithmetic processing unit 22, etc. In more detail, the control unit 25 controls the display panel 8 through the information display circuit 23 and displays information, such as guidance information 31, arrow marks 32, and operating button images 33 illustrated in FIG. 8, on the liquid crystal display screen. Herein, the guidance information 31 is information in the form of characters or images for explaining a manner for electrocardiographic measurement and a posture to be taken in the measurement, for example, to the user.

Further, the control unit 25 controls the display panel 8 through the information display circuit 23 and displays the biological information computed by the arithmetic processing unit 22, e.g., an electrocardiographic waveform based on the electrocardiographic data, on the liquid crystal display screen of the display panel 8.

Moreover, the control unit 25 controls the arithmetic processing unit 22 based on input information entered through the touch panel 9. In more detail, the control unit 25 receives the contact detection signal, which is output from the touch panel 9, through the touch panel drive circuit 24, and detects, based on contact position information included in the contact detection signal, the event that the user's fingers are contacted with the portions of the upper surface of the display window 5 (specifically, the transparent insulating film 12) where the transparent electrodes 10 and 11 are disposed, or that the user's fingers are contacted with the portions of the upper surface of the display window 5 (specifically, the transparent insulating film 12) where the transparent electrodes 10 and 11 are not disposed. Upon detecting that the thumbs of both the user's hands are contacted with the contact surfaces 12A of the transparent insulating film 12 on the transparent electrodes 10 and 11, the control unit 25 controls the arithmetic processing unit 22, etc. and starts the operations of detecting the biological signals from the user's thumbs, generating the electrocardiographic signal, and computing the electrocardiographic data, etc.

The electrocardiographic signal detection device 1 according to the first embodiment of the present invention is constructed as described above. The operation of the electrocardiographic signal detection device 1 will be described below.

Figure 8:
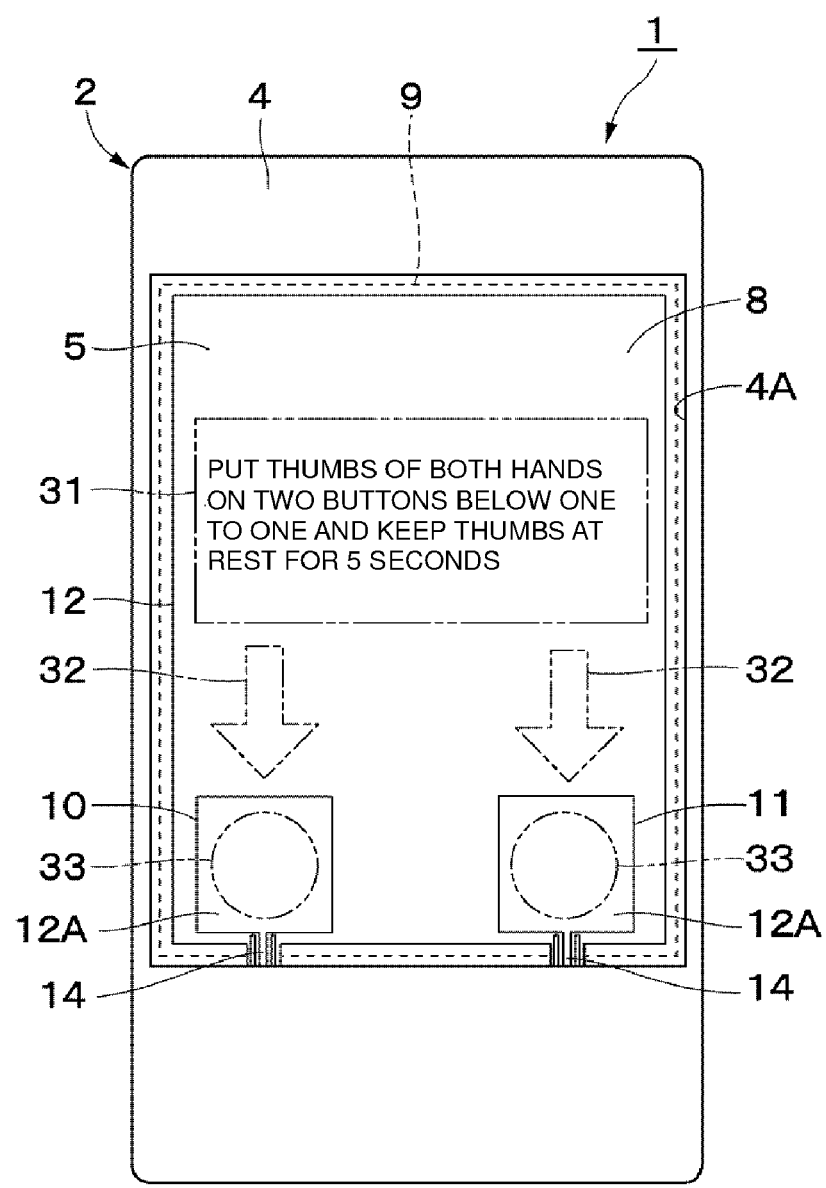
FIG. 8 is a front view of the electrocardiographic signal detection device, illustrating a state where guidance information, etc. are displayed on a screen of a display panel.

First, when the user turns on a power supply for the electrocardiographic signal detection device 1, the control unit 25 controls the display panel 8 through the information display circuit 23 and displays, on the liquid crystal display screen, a menu for allowing the user to selectively start various functions of the electrocardiographic signal detection device 1. Then, when the user touches the display window 5 (specifically, the transparent insulating film 12) and performs an operating action of selecting the electrocardiographic measurement from the menu, the control unit 25 detects the selective operating action through the touch panel 9 and the touch panel drive circuit 24. Subsequently, the control unit 25 operates the display panel 8 through the information display circuit 23 and displays the guidance information 31, the arrow marks 32, and the operating button images 33 on the liquid crystal display screen, as illustrated in FIG. 8.

When the user grasps the electrocardiographic signal detection device 1 by both the hands and brings the thumbs of both the hands into contact with the contact surfaces 12A of the transparent insulating film 12 on the transparent electrodes 10 and 11 as illustrated in FIG. 2, the control unit 25 detects the contacts of the thumbs of both the hands with the contact surfaces 12A through the touch panel 9 and the touch panel drive circuit 24. Further, the control unit 25 controls the arithmetic processing unit 22, etc. and starts the operations of detecting the biological signals from the user's thumbs, generating the electrocardiographic signal, and computing the electrocardiographic data, etc.

As a result, the biological signals varying depending on the activity of the user's heart are detected by the transparent electrodes 10 and 11, respectively. In more detail, the thumbs of both the user's hands, which are contacted with the contact surfaces 12A of the transparent insulating film 12 on the transparent electrodes 10 and 11, and the transparent electrodes 10 and 11 are capacitively coupled to each other, and the biological signals are transferred from the thumbs to the transparent electrodes 10 and 11, respectively. The biological signals having been transferred to the transparent electrodes 10 and 11 are input respectively to the filter units 19 in the processing circuit unit 18 through the current carrying lines 14, the signal terminals of the connectors 16, and the connecting lines 17.

Subsequently, the filter units 19 reduce noises mixed in the biological signals, and the baseline variation suppression unit 20 suppresses variations in respective baselines of the biological signals. The differential amplifier 21 differentially amplifies the two biological signals having been subject to the noise reduction and the suppression of the baseline variations, thereby generating the electrocardiographic signal. Further, the arithmetic processing unit 22 executes arithmetic processing based on the electrocardiographic signal, thereby generating biological information, such as electrocardiographic data. The control unit 25 controls the display panel 8 through the information display circuit 23 to display the biological information (e.g., the electrocardiographic waveform based on the electrocardiographic data) on the liquid crystal display screen.

As described above, the electrocardiographic signal detection device 1 according to the first embodiment of the present invention includes the transparent electrodes 10 and 11 of which upper surfaces are covered with the transparent insulating film 12, and detects the biological signals through capacitive coupling. Therefore, the human fingers, etc. are not directly contacted with the transparent electrodes 10 and 11, and the transparent electrodes 10 and 11 are not exposed to open air. Accordingly, moisture, etc. can be prevented from adhering to the transparent electrodes 10 and 11, and deterioration of the transparent electrodes 10 and 11 can be suppressed. As a result, it is possible to enhance durability of the electrocardiographic signal detection device 1 and to prolong the service life thereof.

Also, in the electrocardiographic signal detection device 1, electrodes for detecting the biological signals are constituted as the transparent electrodes 10 and 11 each made of the transparent material, and the transparent electrodes 10 and 11 are arranged on the upper surface of the display window 5 in overlapped relation to the liquid crystal display screen of the display panel 8. Since the electrodes for detecting the biological signals are constituted as the transparent electrodes, spaces for the arrangement of the electrodes can be secured at positions overlapping with the display panel 8, and flexibility in selecting places where the electrodes are arranged can be increased. Further, since the transparent electrodes 10 and 11 are arranged at the positions overlapping with the display panel 8, a space for arrangement of other components (such as the operating buttons), which are to be arranged on the outer surface of the housing 2, can be easily secured.

Accordingly, the size of the electrocardiographic signal detection device 1 can be reduced as illustrated in FIG. 2. In addition, an area of the display screen of the display panel 8 can be increased, and the degree of freedom in design of the electrocardiographic signal detection device 1 can also be increased.

Moreover, since the transparent electrodes 10 and 11 are arranged on the surface of the display window 5, the guidance information 31, the arrow marks 32, etc. can be displayed adjacent to the transparent electrodes 10 and 11, and the operating button images 33 can be displayed in overlapped relation to the transparent electrodes 10 and 11, as illustrated in FIG. 8. As a result, operability of the electrocardiographic signal detection device 1 can be improved so that even an ordinary person is able to easily perform the electrocardiographic measurement.

For example, the arrow marks 32 and the operating button images 33 can inform the user of the positions where the thumbs are to be placed, and the guidance information 31 can notify the user of, e.g., a time during which the thumbs are to be kept at rest in the state put on the contact surfaces 12A. Therefore, the user can perform the electrocardiographic measurement with no need of carefully reading a manual of the electrocardiographic signal detection device 1.

In the electrocardiographic signal detection device 1, the contact between the user's thumbs and the contact surfaces 12A of the transparent insulating film 12 on the transparent electrodes 10 and 11 is detected through the touch panel 9, and the operations of detecting the biological signals, generating the electrocardiographic signal, and computing the electrocardiographic data, etc. are automatically started in response to the result of the contact detection. As a result, the operability of the electrocardiographic signal detection device 1 can be improved.

The user can start the electrocardiographic measurement just by bringing the thumbs into contact with the contact surfaces 12A of the transparent insulating film 12 on the transparent electrodes 10 and 11. Hence, the user can be avoided from the necessity of performing intricate operations, such as manually starting the measurement and then quickly placing the fingers on the electrodes, or such as placing the fingers on the electrodes and then moving the finger away from the electrode to start the measurement.

Further, the small-sized electrocardiographic signal detection device 1 enables an ordinary person to readily perform the electrocardiographic measurement in daily life. The daily electrocardiographic measurement can be easily promoted by adding the function of a device that is frequently used in daily life, e.g., a cellular phone, a portable terminal, a portable game machine, or a car navigation system, to the electrocardiographic signal detection device 1 (for example, by embodying the present invention as a cellular phone equipped with the function of the electrocardiographic measurement).

The first embodiment has been described above, by way of example, in connection with the case where the two transparent electrodes 10 and 11 are arranged within the upper surface of the display window 5 in its forward-side portion closer to the user. Such a layout is desirable for the reason that the user can positively make the thumbs of the both hands contacted with the contact surfaces 12A of the transparent insulating film 12 on the transparent electrodes 10 and 11, respectively, while grasping the electrocardiographic signal detection device 1 by both the hands. However, the number of the transparent electrodes and the arrangement positions thereof are not limited to those described in the first embodiment.

Portions of the human body, which are contacted with the contact surfaces 12A of the transparent insulating film 12 on the transparent electrodes 10 and 11, are not limited to the thumbs, and the forefingers, the middle fingers, or the palms may be contacted with the contact surfaces 12A. The number of the transparent electrodes and the arrangement positions thereof may be set, as appropriate, depending on the portions of the human body, which are contacted with the contact surfaces 12A of the transparent insulating film 12. Also, the first embodiment has been described above, by way of example, in connection with the case where the transparent insulating film 12 is coated over not only the upper surfaces of the transparent electrodes 10 and 11, but also the remaining portion of the upper surface of the display window 5 where the transparent electrodes 10 and 11 are not formed. However, the present invention is not limited to such an arrangement. The transparent insulating film 12 may be disposed only over the upper surfaces of the transparent electrodes 10 and 11.

Further, the first embodiment has been described above, by way of example, in connection with the case where the display panel 8 having the liquid crystal display screen is employed. However, a plasma display panel, an organic EL (Electroluminescence) display panel, an inorganic EL display panel, a field emission display panel, an MEMS (Micro Electro Mechanical System) display panel, or an electronic paper, or the like may also be employed instead of the display panel 8.

Figure 9:
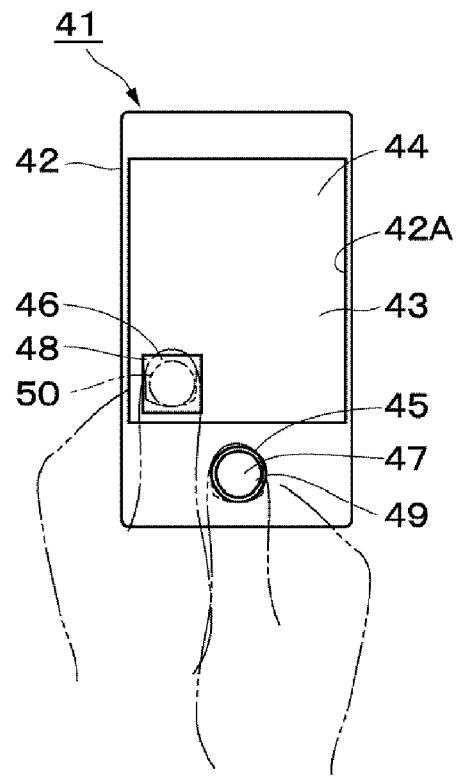
FIG. 9 is an explanatory view of an electrocardiographic signal detection device according to a second embodiment in a state where the electrocardiographic measurement is performed.

A second embodiment of the present invention will be described below with reference to FIG. 9. As illustrated in FIG. 9, an electrocardiographic signal detection device 41 according to the second embodiment of the present invention includes a housing 42 made of an insulating material, e.g., resin. A display window 43 is attached to an opening 42A formed in an upper surface of the housing 42, and a display panel 44 is disposed under the display window 43. An operating button 45 made of an insulating material, e.g., resin, is disposed on the upper surface of the housing 42.

The electrocardiographic signal detection device 41 further includes two electrodes 46 and 47 for detecting the biological signals. One electrode 46 is a transparent electrode similar to the transparent electrode 10 in the first embodiment and is arranged within an upper surface of the display window 43 in a forward left portion thereof closer to the user. An insulating film 48 made of a transparent insulating material is coated on an upper surface of the electrode 46, and one surface of the transparent insulating film 48, which is positioned oppositely away from the other surface being in contact with the electrode 46, serves as a contact surface that is to be contacted with the human thumb.

The other electrode 47 is an electrode made of a transparent or opaque electroconductive material and is arranged on the surface of the operating button 45. An insulating film 49 made of a transparent or opaque insulating material is coated on an upper surface of the electrode 47, and one surface of the transparent insulating film 49, which is positioned oppositely away from the other surface being in contact with the electrode 47, serves as a contact surface that is to be contacted with the human thumb. Each of the electrodes 46 and 47 detects the biological signal from the human thumb through capacitive coupling.

Further, a processing circuit unit (not shown) similar to the processing circuit unit 18 illustrated in FIG. 7 is contained inside the housing 42. The processing circuit unit has the function of, when the operating button 45 is pressed, starting the operations of detecting the biological signals, generating the electrocardiographic signal, and computing the electrocardiographic data, etc.

The processing circuit unit displays, at a position on a display screen of the display panel 44 corresponding to the electrode 46, a mark 50 indicating that the relevant position is a place where the thumb of the user's left hand is to be put for contact with the electrode 46. In addition, the processing circuit unit displays, on the display screen of the display panel 44, guidance information (not shown), such as "PUT THUMB OF LEFT HAND ON MARK BELOW. PUT THUMB OF RIGHT HAND ON OPERATING BUTTON AND PRESS OPERATING BUTTON. THEN, KEEP BOTH THUMBS AT REST FOR 5 SECONDS".

The electrocardiographic signal detection device 41 according to the second embodiment of the present invention is constructed as described above. The operation of the electrocardiographic signal detection device 41 will be described below. In accordance with the guidance information, etc. displayed on the display screen of the display panel 44, the user brings the thumbs of both the hands into contact with the contact surface of the insulating film 48 on the electrode 46 and the contact surface of the insulating film 49 on the electrode 47, respectively, and then presses the operating button 45 by the thumb contacting with the contact surface of the insulating film 49. Upon the operating button 45 being pressed, the operations of detecting the biological signals, generating the electrocardiographic signal, and computing the electrocardiographic data, etc. are started. Further, the electrocardiographic waveform, etc. based on the computed electrocardiographic data are displayed on the display screen of the display panel 44.

With the electrocardiographic signal detection device 41 according to the second embodiment of the present invention, as described above, since the insulating films 48 and 49 are coated respectively on the electrodes 46 and 47 for detecting the biological signals, deterioration of the electrodes 46 and 47 can be suppressed and durability of the electrocardiographic signal detection device 41 can be enhanced.

Also, since the electrode 46 and the insulating film 48 are formed to be transparent and are arranged on the upper surface of the display window 43 at a position overlapping with the display panel 44, the size of the electrocardiographic signal detection device 41 can be reduced.

Further, since the electrode 47 is arranged on the operating button 45, operability of the electrocardiographic signal detection device 41 can be improved. For example, the user can start the electrocardiographic measurement by pressing the operating button 45 while keeping the thumbs in a state contacted with the insulating films 48 and 49 on the electrodes 46 and 47.

The second embodiment has been described above, by way of example, in connection with the case where the electrode 47 is arranged on the operating button 45. However, the electrode 47 may be buried instead inside the operating button 45. In that case, a portion of the upper surface of the operating button 45, which covers an upper surface of the buried electrode 47, corresponds to the insulating film 49.

Figure 10:
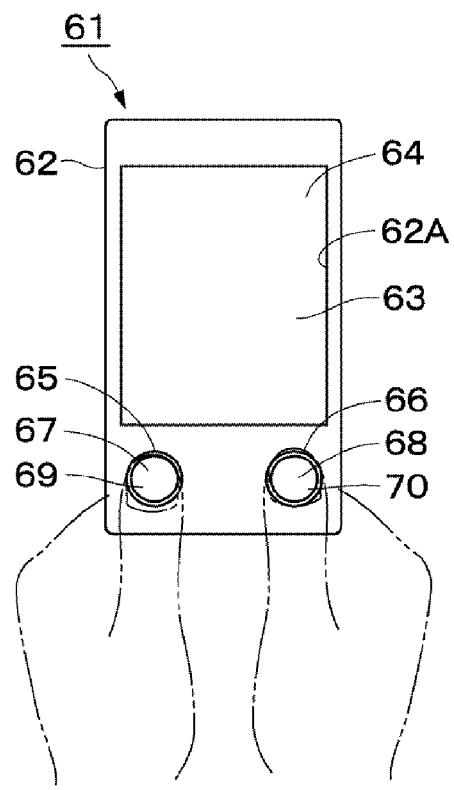
FIG. 10 is an explanatory view of an electrocardiographic signal detection device according to a third embodiment in a state where the electrocardiographic measurement is performed.

A third embodiment of the present invention will be described below with reference to FIG. 10. As illustrated in FIG. 10, an electrocardiographic signal detection device 61 according to the third embodiment of the present invention includes a housing 62 made of an insulating material, e.g., resin. A display window 63 is attached to an opening 62A formed in an upper surface of the housing 62, and a display panel 64 is disposed under the display window 63. Operating buttons 65 and 66 each made of an insulating material, e.g., resin, are disposed on the upper surface of the housing 62.

Two electrodes 67 and 68 for detecting the biological signals are disposed respectively on upper surfaces of the operating buttons 65 and 66. The electrodes 67 and 68 are each made of a transparent or opaque electroconductive material. Insulating films 69 and 70 each made of a transparent or opaque insulating material are coated respectively on upper surfaces of the electrodes 67 and 68. One respective surfaces of the insulating film 69 and 70, which are positioned oppositely away from the other surfaces being in contact with the electrodes 67 and 68, serve as contact surfaces that are to be contacted with the human thumbs. The electrodes 67 and 68 detect the biological signals of the human body through capacitive coupling between the human thumbs contacting with the contact surfaces of the insulating films 69, 70 and the electrodes 67, 68.

Further, a processing circuit unit (not shown) similar to the processing circuit unit 18 illustrated in FIG. 7 is contained inside the housing 62. The processing circuit unit has the function of, when the operating button 65 or 66 is pressed, starting the operations of detecting the biological signals, generating the electrocardiographic signal, and computing the electrocardiographic data, etc.

With the electrocardiographic signal detection device 61 according to the third embodiment of the present invention, as described above, since the insulating films 69 and 70 are coated respectively on the upper surfaces of the electrodes 67 and 68, deterioration of the electrodes 67 and 68 can be suppressed and durability of the electrocardiographic signal detection device 61 can be enhanced.

Also, since the electrodes 67 and 68 are arranged on the upper surfaces of the operating buttons 65 and 66, the user can start the electrocardiographic measurement by pressing the operating button 65 or 66 while keeping the thumbs in a state contacted with the insulating films 69 and 70 on the electrodes 67 and 68. As a result, operability of the electrocardiographic signal detection device 61 can be improved.

The third embodiment has been described above, by way of example, in connection with the case where the electrodes 67 and 68 are arranged respectively on the upper surfaces of the operating buttons 65 and 66. However, the electrodes 67 and 68 may be buried instead inside the operating button 65 and 66. In that case, portions of the upper surfaces of the operating buttons 65 and 66, which cover the upper surfaces of the buried electrodes 67 and 68, correspond to the insulating films 69 and 70, respectively.

Also, the third embodiment has been described above, by way of example, in connection with the case where the electrodes 67 and 68 are arranged respectively on the upper surfaces of the operating buttons 65 and 66. However, the present invention is not limited to that arrangement. For example, the third embodiment may be modified such that the operating button 65 is omitted, the electrode 67 is formed directly on an upper surface of the housing 62, and the insulating film 69 is coated on the thus-formed electrode 67.

As an alternative, the operating button 65 may be omitted and the electrode 67 may be buried in the upper surface of the housing 62. In that case, a portion of the upper surface of the housing 62, which covers an upper surface of the buried electrode 67, corresponds to the insulating film 69.

Figure 11:
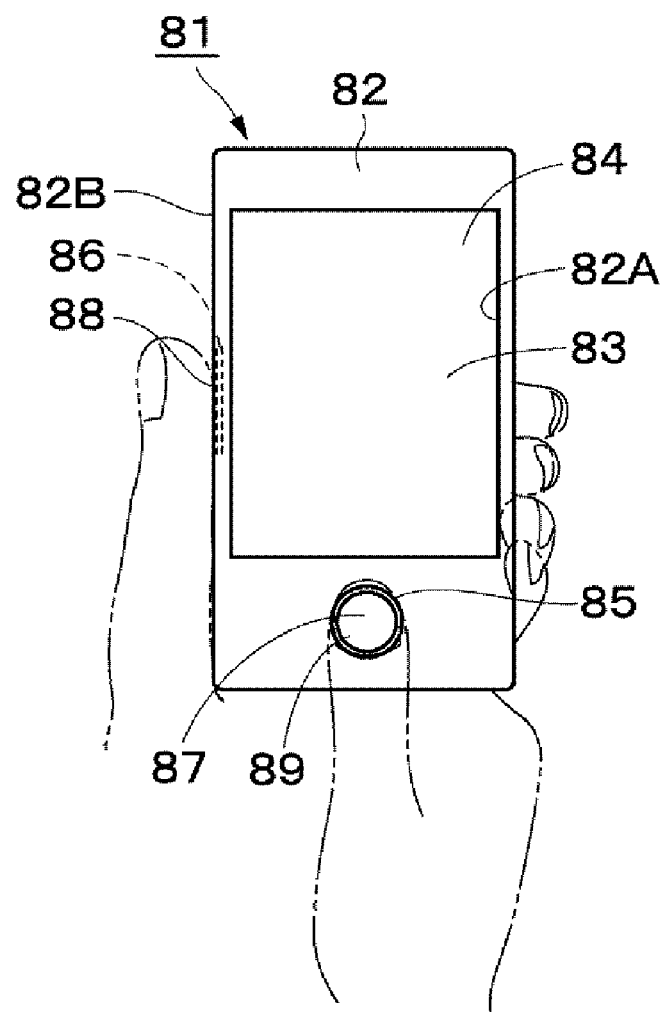
FIG. 11 is an explanatory view of an electrocardiographic signal detection device according to a fourth embodiment in a state where the electrocardiographic measurement is performed.

A fourth embodiment of the present invention will be described below with reference to FIG. 11. As illustrated in FIG. 11, an electrocardiographic signal detection device 81 according to the fourth embodiment of the present invention includes a housing 82 made of an insulating material, e.g., resin. A display window 83 is attached to an opening 82A formed in an upper surface of the housing 82, and a display panel 84 is disposed under the display window 83. An operating button 85 made of an insulating material is disposed on the upper surface of the housing 82.

One 86 of two electrodes 86 and 87 for detecting the biological signals is buried in a left side panel 82B of the housing 82. An insulating portion 88 of the housing 82, which covers an upper surface (i.e., a surface directing leftward in FIG. 11) of the electrode 86 buried in the left side panel 82B, corresponds to an insulating film that is coated on the electrode.

The other electrode 87 is arranged on an upper surface of the operating button 85, and an insulating film 89 is coated on the electrode 87. As an alternative, the electrode 87 may be buried in the operating button 85.

The thus-constructed fourth embodiment of the present invention can provide substantially the same advantageous effects as those in the above-described second embodiment. In particular, since the one electrode 86 is arranged in the left side surface of the housing 82, the user can make the thumb of the left hand contacted with the insulating portion 88 on the one electrode 86, as illustrated in FIG. 11, while grasping the electrocardiographic signal detection device 81 from the bottom side by the left hand. Accordingly, the user can perform the electrocardiographic measurement in a more stable posture.

A fifth embodiment of the present invention will be described below with reference to FIGS. 12 to 18. Be it noted that the same components in the fifth embodiment as those in the first embodiment are denoted by the same symbols and description of those components is omitted.

Figure 12:
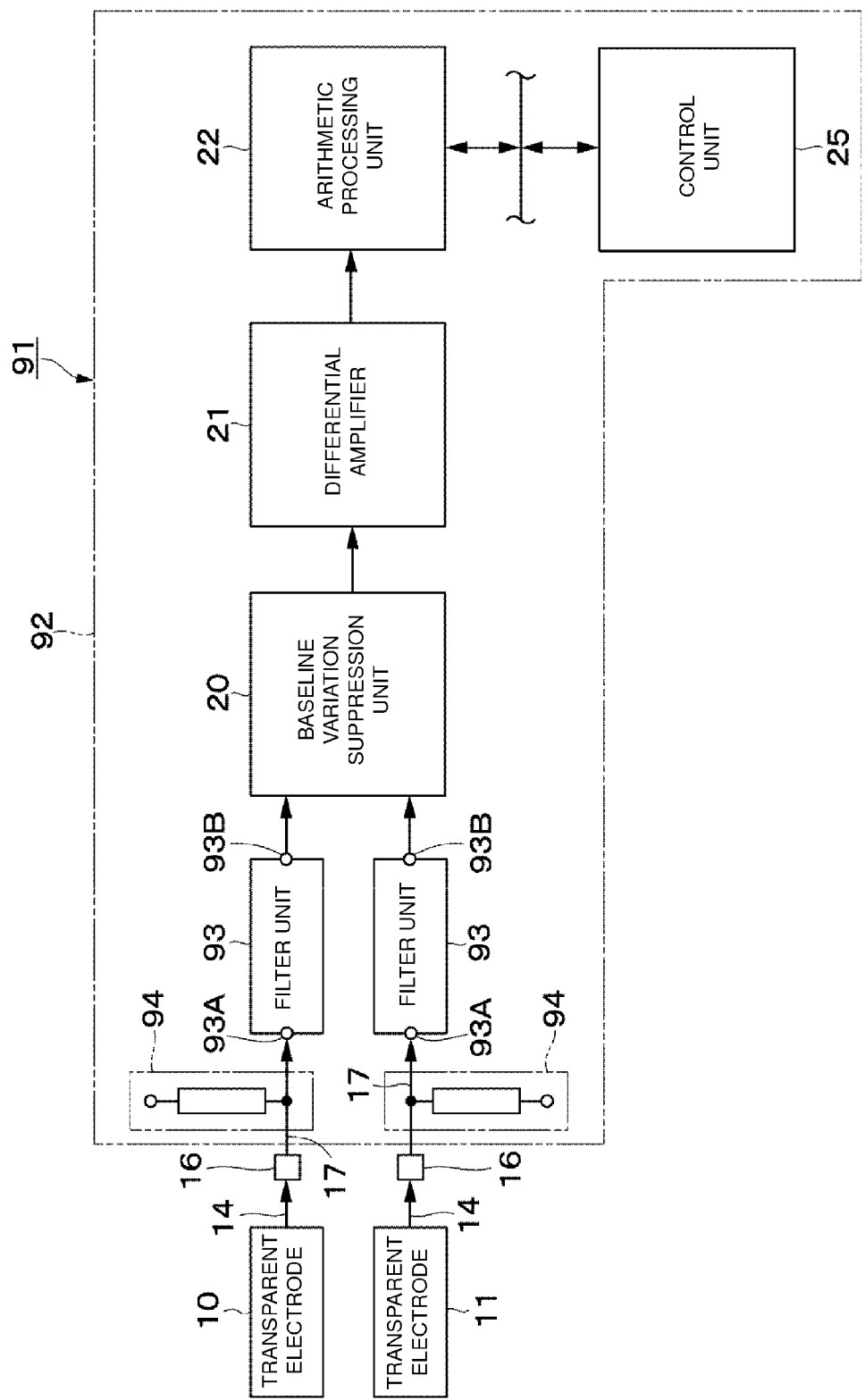
FIG. 12 is a circuit diagram illustrating the electrical configuration of an electrocardiographic signal detection device according to a fifth embodiment.

As illustrated in FIG. 12, an electrocardiographic signal detection device 91 according to the fifth embodiment of the present invention includes a processing circuit unit 92. As in the processing circuit unit 18 in the first embodiment, the processing circuit unit 92 includes two filter units 93 (described below), the baseline variation suppression unit 20, the differential amplifier 21, the arithmetic processing unit 22, the control unit 25, etc.

The filter units 93 are disposed in the input terminal side of the processing circuit unit 92. In more detail, input terminals 93A of the filter units 93 are connected respectively to the transparent electrodes 10 and 11 through the current carrying lines 14, the signal terminals of the connectors 16, and the connecting lines 17. Also, output terminals 93B of the filter units 93 are connected respectively to input terminals of the differential amplifier 21 through the baseline variation suppression unit 20. The filter units 93 reduce noises in the biological signals that are detected through capacitive coupling between the human thumbs and the transparent electrodes 10, 11 when the human thumbs are brought into contact with the contact surfaces 12A of the transparent insulating film 12 on the transparent electrodes 10 and 11.

Figure 13:
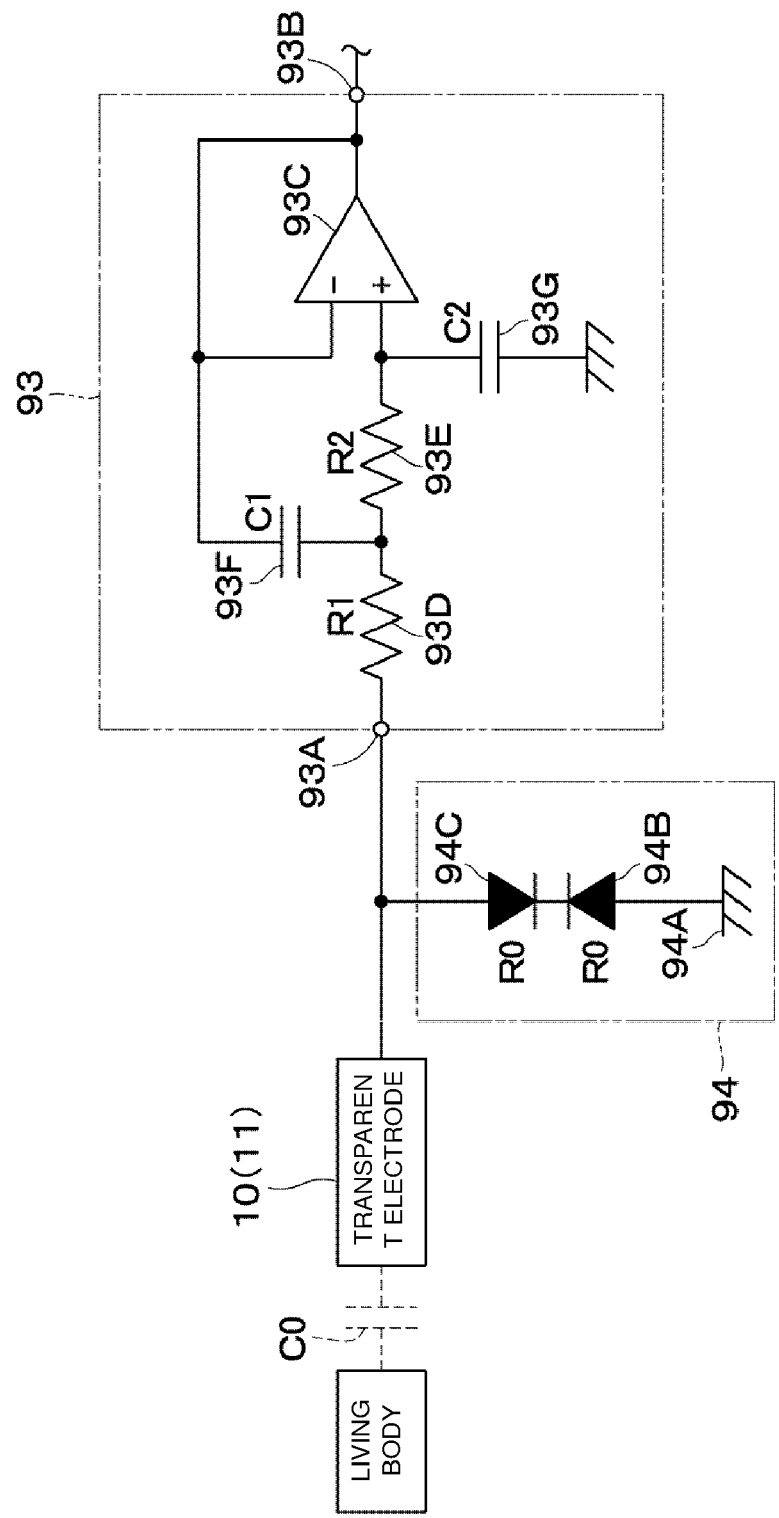
FIG. 13 is a circuit diagram illustrating a filter unit, a clamp circuit, etc.

The filter units 93 are each constituted by, e.g., a low-pass filter (LPF). In more detail, as illustrated in FIG. 13, the filter units 93 are each constituted, for example, by a Sallen-Key circuit including an operational amplifier 93C, first and second resistances 93D and 93E connected in series between a non-inverting terminal of the operational amplifier 93C and the input terminal 93A, a first capacitor 93F connected between a junction between the first and second resistances 93D, 93E and an output terminal of the operational amplifier 93C, and a second capacitor 93G connected between the non-inverting terminal of the operational amplifier 93C and a ground. An inverting terminal and the output terminal of the operational amplifier 93C are connected to each other. In such a configuration, the cutoff frequency of the filter unit 93 is determined depending on resistance values R1 and R2 of the resistances 93D and 93E and capacity values C1 and C2 of the capacitors 93F and 93G.

A clamp circuit 94 is connected to the input terminal 93A of the filter unit 93. The clamp circuit 94 includes a ground 94A serving as a DC constant-voltage source, and diodes 94B and 94C each connected between the ground 94A and the input terminal 93A and serving as a high-impedance element. In such a configuration, the diodes 94B and 94C are connected in series in a mutually confronting state such that forward directions of the diodes are opposed to each other. Thus, cathodes of the diodes 94B and 94C are connected to each other, an anode of the diode 94B is connected to the ground 94A, and an anode of the diode 94C is connected to the input terminal 93A.

Therefore, the diode 94B has a reverse characteristic for an electrical signal at a voltage higher than the ground voltage and serves as a high-impedance element having a resistance value R0 of, e.g., 100 MΩ or more. On the other hand, the diode 94C has a reverse characteristic for an electrical signal at a voltage lower than the ground voltage and serves as a high-impedance element having a resistance value R0 of, e.g., 100 MΩ or more. The clamp circuit 94 fixedly holds a reference potential at the input terminal 93A, i.e., at the connected end of the clamp circuit 94, to be constant as the ground voltage.

Herein, the impedance when looking at the differential amplifier 21 from the connected end of the clamp circuit 94 is set to a value larger than the impedance (resistance value R0) of the clamp circuit 94. In more detail, the impedance of the clamp circuit 94 is primarily determined by the resistance value R0 in the reverse characteristics of the diodes 94B and 94C. Also, the resistance value R0 is generally set to a value smaller than 1 GΩ or more that is the input impedance at the non-inverting terminal (input terminal) of the operational amplifier 93C in the filter unit 93. Accordingly, the impedance when looking at the differential amplifier 21 from the transparent electrodes 10 and 11 is determined by the resistance value R0 of the diodes 94B and 94C.

In view of the above point, the resistance value R0 of the diodes 94B and 94C will be discussed below. When the biological signals are measured through capacitive coupling between the living body and the transparent electrodes 10, 11 as in the electrocardiographic signal detection device 91, a loss caused at the input terminal 93A of each filter unit 93 depends on an electrostatic capacity value C0 between the living body and each of the transparent electrodes 10, 11 and the resistance value R0 of the clamp circuit 94. Therefore, unless the electrostatic capacity value C0 and the resistance value R0 are appropriately selected, a loss is caused in a frequency band of the biological signal.

In this embodiment, each of the transparent electrodes 10 and 11 has a size comparable to that of a finger tip, i.e., a contact portion of the living body. Accordingly, the transparent electrodes 10 and 11 are each in a rectangular shape with one side having a length of about 10 mm to 30 mm or an elliptic shape with a diameter of about 10 mm to 30 mm. Further, the transparent electrodes 10 and 11 are each covered with the transparent insulating film 12 having a thickness of about several μm to several tens μm. Hence, the electrostatic capacity value C0 generated between the living body and each of the transparent electrodes 10, 11 is about 70 pF to 600 pF.

In order to enable the biological signal to be detected with respect to the electrostatic capacity value C0, it is required to reduce distortion of the waveform of the biological signal and to reduce the influence of radiation noise. Those requirements are satisfied when the resistance value R0 is larger than a value indicated by a boundary line X in FIG. 14. In other words, those requirements are satisfied when the resistance value R0 falls within a region B in FIG. 14.

Figure 14:
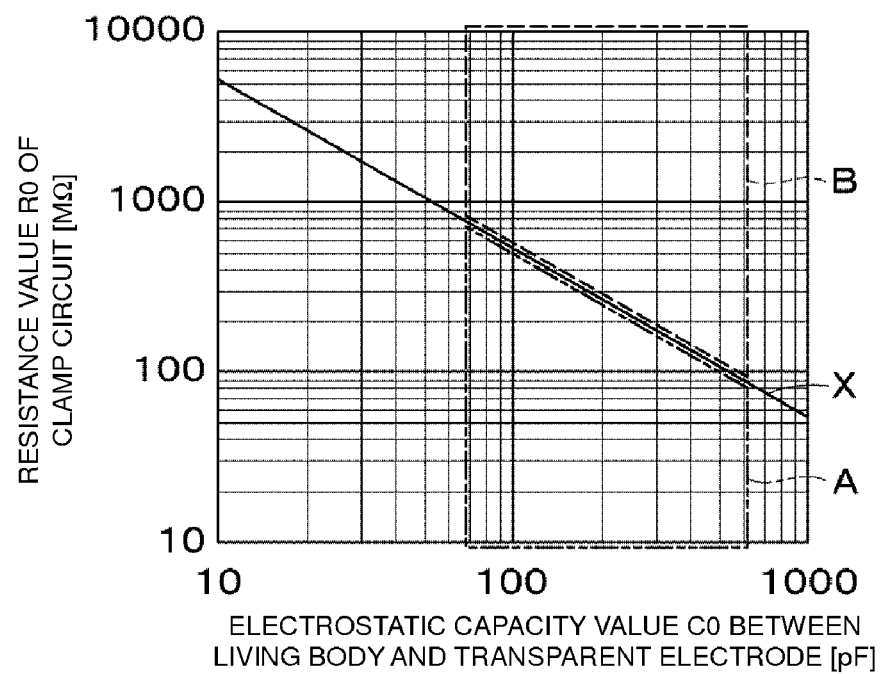
FIG. 14 is a graph to explain the relationship of an electrostatic capacity value between a living body and the transparent electrode versus a resistance value of the clamp circuit.
Figure 15:
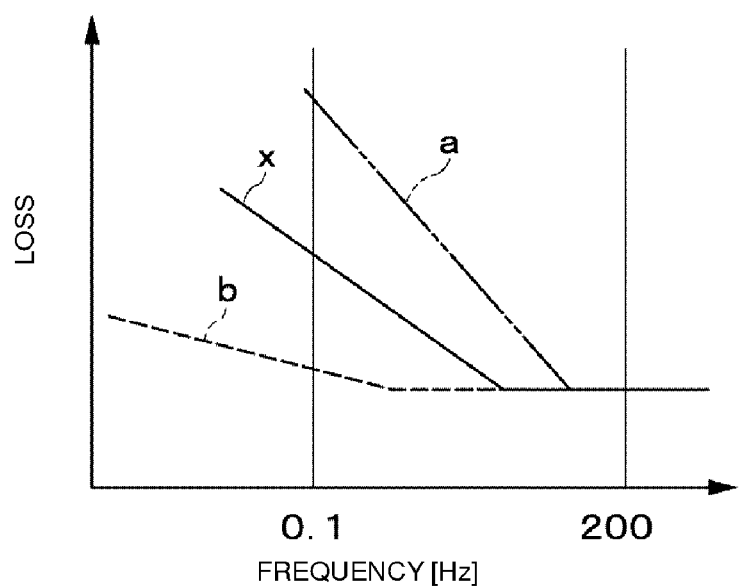
FIG. 15 is a frequency characteristic graph plotting the relationship between a signal loss in an input portion of the electrocardiographic signal detection device and a frequency of a biological signal.
Figure 16:
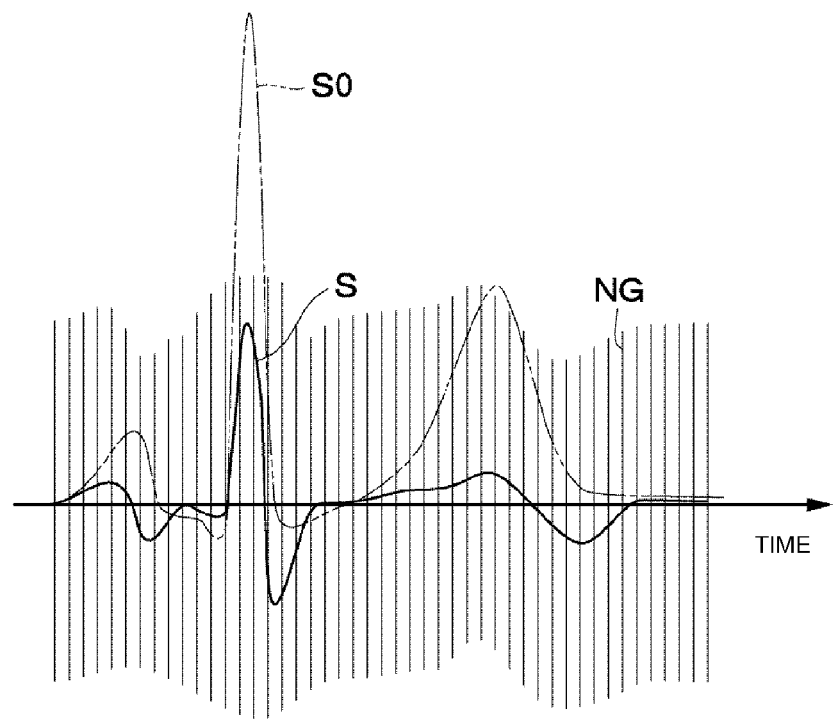
FIG. 16 is a characteristic line chart indicating changes over time of the biological signal and radiation noise when the resistance value of the clamp circuit is within a region A in FIG. 14.

More specifically, when the resistance value R0 falls within a region A in FIG. 14, the loss in a frequency band of 0.1 to 200 Hz of the biological signal is increased as represented by a characteristic line a in FIG. 15. In that case, as illustrated in FIG. 16, distortion of a biological signal S is increased in comparison with an ideal biological signal S0 having no loss, and an appropriate biological signal cannot be detected.

Figure 17:
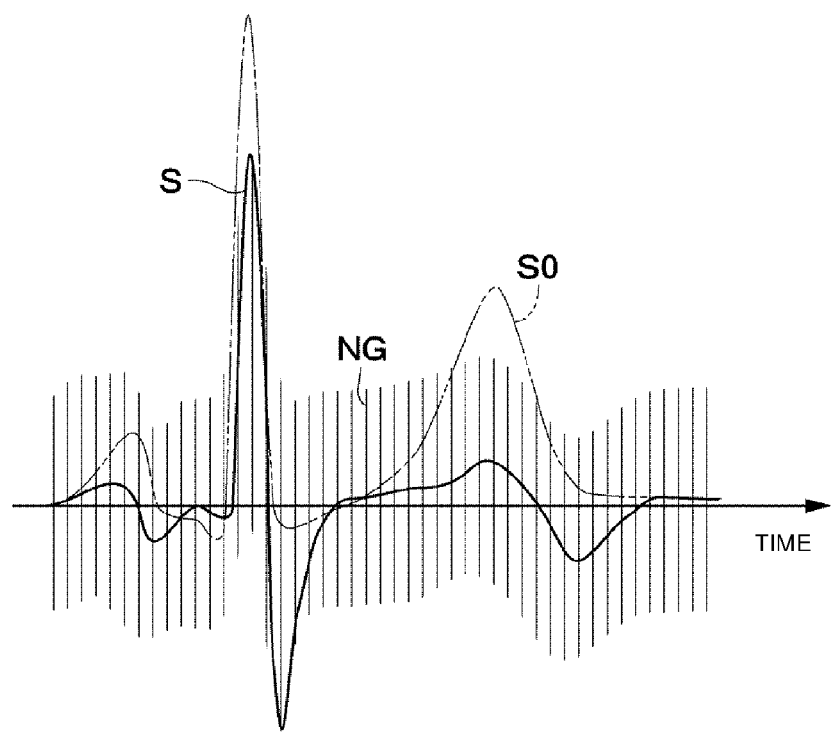
FIG. 17 is a characteristic line chart indicating changes over time of the biological signal and radiation noise when the resistance value of the clamp circuit is near a boundary line X in FIG. 14.

On the other hand, when the resistance value R0 is near the boundary line X in FIG. 14, the loss in the frequency band of 0.1 to 200 Hz of the biological signal is reduced as represented by a characteristic line x in FIG. 15. In that case, as illustrated in FIG. 17, the distortion of the biological signal S is reduced and the waveform of the biological signal S comes closer to that of the ideal biological signal S0. Further, since the resistance value R0 is larger than that in the region A, the influence of radiation noise NG is reduced. Accordingly, it is difficult to detect the detailed waveform of the biological signal, but a peak of the biological signal can be detected.

Figure 18:
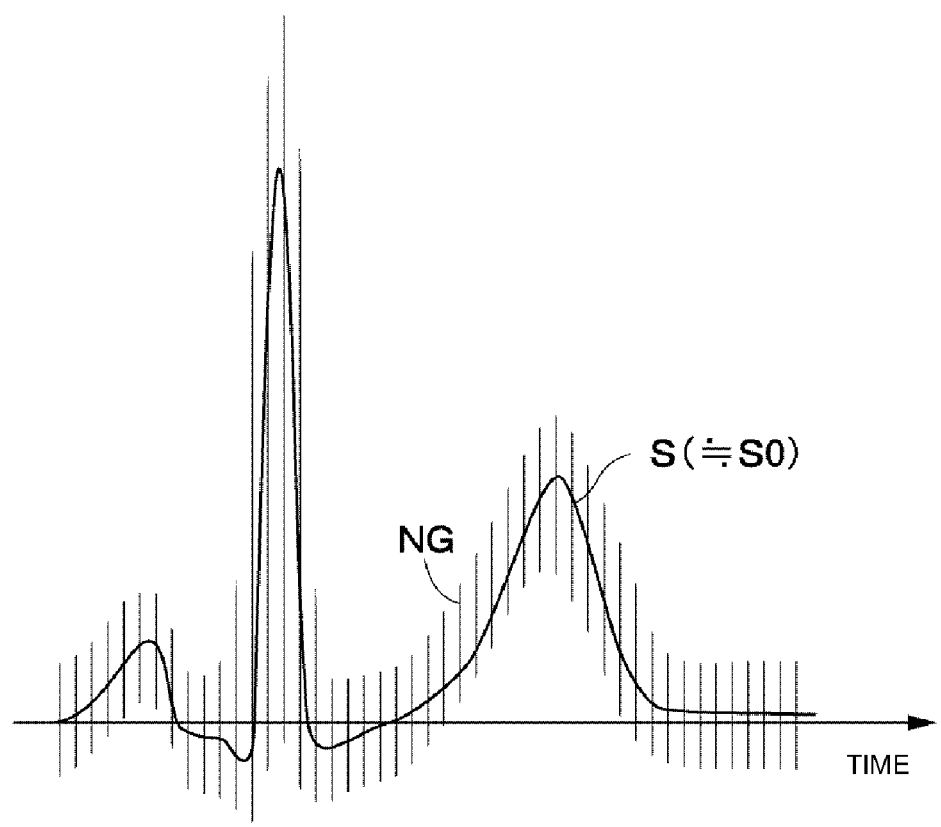
FIG. 18 is a characteristic line chart indicating changes over time of the biological signal and radiation noise when the resistance value of the clamp circuit is within a region B in FIG. 14.

When the resistance value R0 falls within the region B in FIG. 14, the loss in the frequency band of 0.1 to 200 Hz of the biological signal is further reduced as represented by a characteristic line b in FIG. 15. In that case, as illustrated in FIG. 18, the waveform of the biological signal S is changed substantially in the same manner as that of the ideal biological signal S0, and the distortion of the biological signal S and the influence of the radiation noise NG are further reduced. Consequently, the resistance value R0 needs to be held within the region B in FIG. 14 in order to reduce both the distortion of the biological signal and the influence of the radiation noise NG. In other words, the resistance value R0 requires to be, e.g., 100 MΩ or more.

In the case of an ordinary resistance element used in a clamp circuit, a resistance value is about several MΩ at maximum and a high impedance at the above-mentioned level of 100 MΩ or more cannot be obtained. Therefore, when the ordinary resistance element is used, the distortion of the biological signal S is increased and the SN ratio is reduced. On the other hand, in the clamp circuit 94 according to this embodiment, the high impedance of 100 MΩ or more is realized as the resistance value R0 by utilizing the reverse characteristics of the diodes 94B and 94C.

More specifically, in this embodiment, the voltages of the biological signals generated depending the sizes of the transparent electrodes 10 and 11 are each about 1 to 2 mV. In that case, when the diodes 94B and 94C are connected to each other in oppositely faced relation as illustrated in FIG. 13, the generated voltage of 1 to 2 mV is applied as a reverse voltage to one of the diodes 94B and 94C due to the reverse characteristic thereof. However, the breakdown voltage of each of the diodes 94B and 94C is usually about 1 V. Thus, since the reverse voltage is sufficiently lower than the breakdown voltage, no electric currents flow through the diodes 94B and 94C. As a result, each of the diodes 94B and 94C functions as the high-impedance element of, e.g., 100 MΩ or more. In this embodiment, therefore, the biological signal S can be detected as a satisfactory signal having smaller distortion and a higher SN ratio.

The externally mixed radiation noise NG primarily includes noise (50 Hz or 60 Hz) from a commercial power supply and noises (200 Hz or higher) at higher harmonics of the commercial frequency (i.e., at integer multiples of 50 Hz or 60 Hz). The noise from the commercial power supply is applied to the two transparent electrodes 10 and 11 in the same phase, and hence the noises detected through the two transparent electrodes 10 and 11 are canceled off by the differential amplifier 21. The other noises of 200 Hz or higher are removed by the filter units 93. Accordingly, the cutoff frequency of each of the filter units 93 is set to an appropriate value of 200 Hz or higher.

The thus-constructed fifth embodiment of the present invention can provide substantially the same advantageous effects as those in the above-described first embodiment. In trying to detect the biological signal through the capacitive coupling between each of the transparent electrodes 10, 11 and the living body, if the impedance when looking at the differential amplifier 21 from the transparent electrodes 10 and 11 is low, the loss in the frequency band of the biological signal is increased and the biological signal cannot be detected. Also, if the reference potential at the input terminal 93A of the filter unit 93 is not fixedly held, variations in a central potential of the biological signal are increased and stable measurement of the biological signal is difficult to realize. In contrast, according to the fifth embodiment, since the reference potential at the input terminal 93A of the filter unit 93, which is positioned in the stage upstream of the input terminal of the differential amplifier 21, can be fixedly held by the clamp circuit 94, variations in the central potential of the biological signal can be reduced.

Further, since the clamp circuit 94 is constituted by the diodes 94B and 94C each serving as the high-impedance element and the impedance when looking at the input terminal of the differential amplifier 21 from the connected end of the clamp circuit 94 is set to be larger than the impedance (resistance value R0) of the clamp circuit 94, the loss in the frequency band of the biological signal can be reduced. In addition, since the reference potential on the side upstream of the differential amplifier 21 can be fixedly held by the clamp circuit 94, variations in the central potential of the biological signal are reduced. As a result, the SN ratio is improved and the biological signal can be stably detected.

A sixth embodiment of the present invention will be described below with reference to FIGS. 19 and 20. Be it noted that the same components in the sixth embodiment as those in the first embodiment are denoted by the same symbols and description of those components is omitted.

Figure 19:
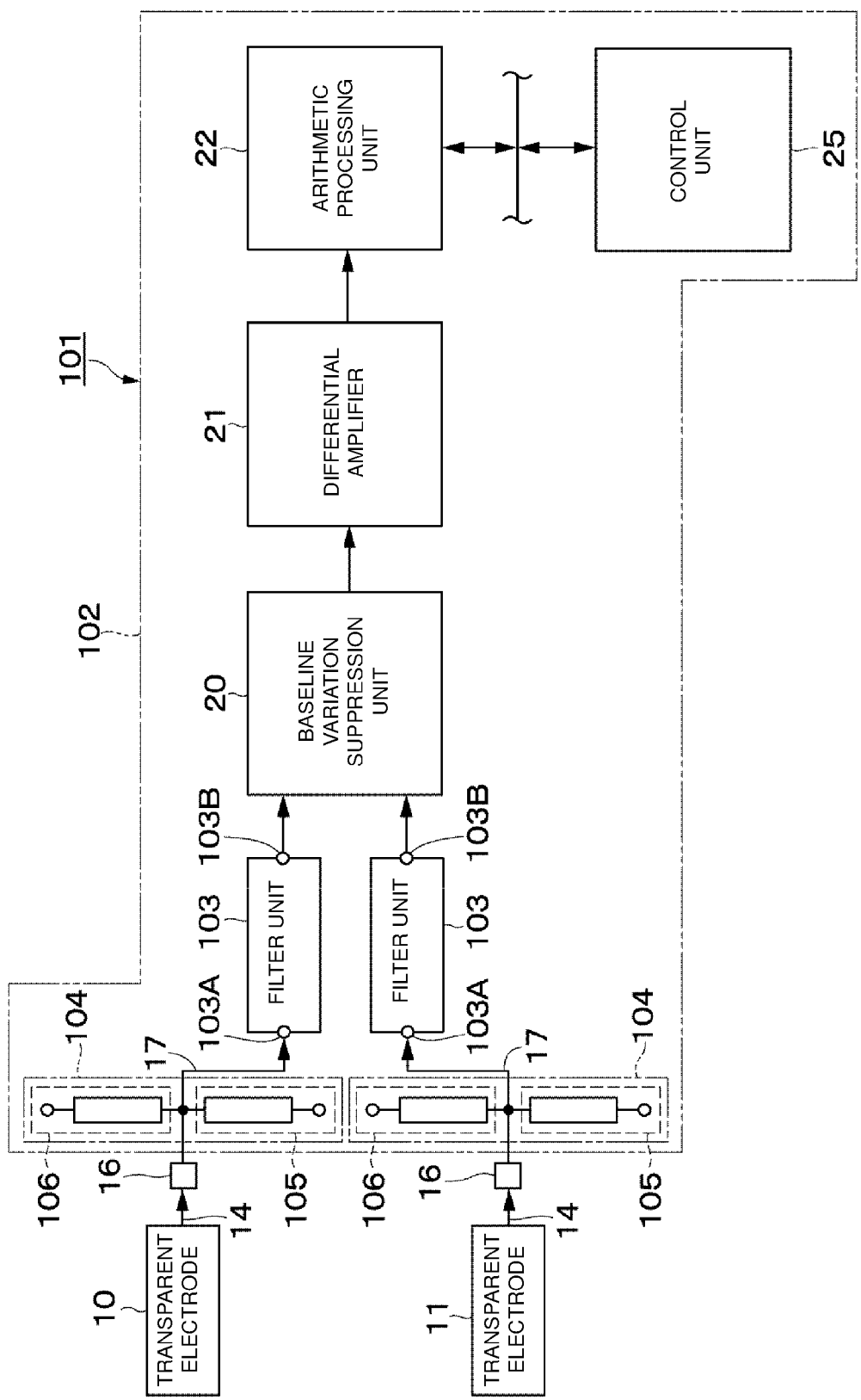
FIG. 19 is a circuit diagram illustrating the electrical configuration of an electrocardiographic signal detection device according to a sixth embodiment of the present invention.

As illustrated in FIG. 19, an electrocardiographic signal detection device 101 according to the fourth embodiment of the present invention includes a processing circuit unit 102. As in the processing circuit unit 18 in the first embodiment, the processing circuit unit 102 includes two filter units 103, the baseline variation suppression unit 20, the differential amplifier 21, the arithmetic processing unit 22, the control unit 25, etc.

Input terminals 103A of the filter units 103 are connected respectively to the transparent electrodes 10 and 11, and output terminals 103B of the filter units 103 are connected respectively to the input terminals of the differential amplifier 21 through the baseline variation suppression unit 20. Further, almost like the filter units 93 in the fifth embodiment, for example, the filter units 103 are each in the form of a low-pass filter that is constituted by a Sallen-Key circuit including an operational amplifier 103C, first and second resistances 103D and 103E, and first and second capacitors 103F and 103G. The filter units 103 are disposed in the input terminal side of the processing circuit unit 102 and reduce noises in the biological signals.

A clamp circuit unit 104 is connected to the input terminal 103A of each of the filter units 103. The clamp circuit unit 104 includes two first and second clamp circuits 105 and 106.

Figure 20:
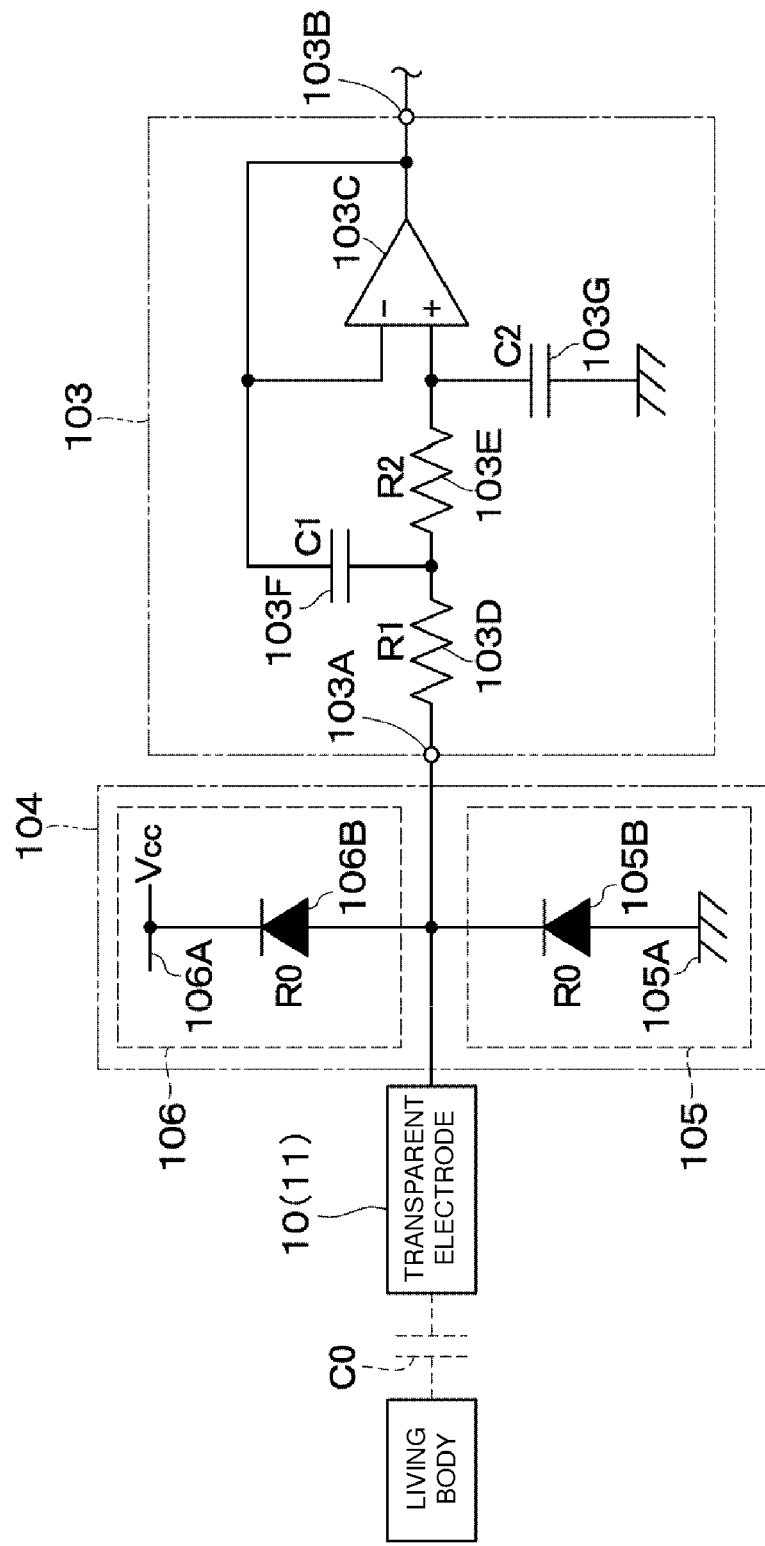
FIG. 20 is a circuit diagram illustrating a filter unit, a clamp circuit, etc.

As illustrated in FIG. 20, the first clamp circuit 105 includes a ground 105A serving as a first DC constant-voltage source, and a diode 105B connected between the ground 105A and the input terminal 103A and serving as a first high-impedance element. In such a configuration, an anode of the diode 105B is connected to the ground 105A, and a cathode of the diode 105B is connected to the input terminal 103A. Therefore, the diode 105B has a reverse characteristic for an electrical signal at a voltage higher than the ground voltage and serves as a high-impedance element having a resistance value R0 of, e.g., 100 MΩ or more.

On the other hand, the second clamp circuit 106 includes, e.g., a drive voltage source 106A for the operational amplifier 103C, which serves as a second DC constant-voltage source, and a diode 106B connected between the drive voltage source 106A and the input terminal 103A and serving as a second high-impedance element. In such a configuration, an anode of the diode 106B is connected to the input terminal 103A, and a cathode of the diode 106B is connected to the drive voltage source 106A. Therefore, the diode 106B has a reverse characteristic for an electrical signal at a voltage lower than a drive voltage Vcc provided by the drive voltage source 106A and serves as a high-impedance element having a resistance value R0 of, e.g., 100 MΩ or more.

Herein, the impedance when looking at the differential amplifier 21 from connected ends of the clamp circuits 105 and 106 is set to a value larger than the impedance (resistance value R0) of the clamp circuits 105 and 106. In more detail, the resistance value R0 in the reverse characteristics of the diodes 105B and 106B, which defines the impedance of each of the clamp circuits 105 and 106, is set to a value smaller than 1 GΩ or more that is the input impedance at a non-inverting terminal (input terminal) of the operational amplifier 103C in the filter unit 103.

The clamp circuits 105 and 106 fixedly hold a reference potential at the input terminal 103A, i.e., at the connected ends of the clamp circuits 105 and 106, to a constant voltage that is determined in advance between the drive voltage Vcc and the ground voltage.

The thus-constructed sixth embodiment of the present invention can provide substantially the same advantageous effects as those in the above-described first and fifth embodiments. In particular, with the sixth embodiment, since the plural clamp circuits 105 and 106 are connected to the input terminal 103A of the filter unit 103, the reference potential at the input terminal 103A of the filter unit 103 can be set to any desired value between the ground voltage in the first clamp circuit 105 and the drive voltage Vcc in the second clamp circuit 106. Consequently, the reference potential at the input terminal 103A of the filter unit 103 can be set to an appropriate value in consideration of an amplifiable range of the operational amplifier 103C in the filter unit 103, the magnitude of the biological signal, and so on.

Figure 21:
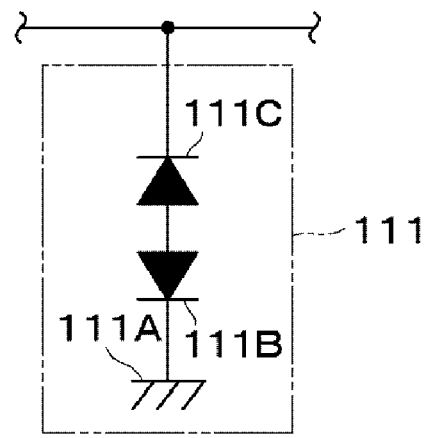
FIG. 21 is a circuit diagram illustrating a clamp circuit in a seventh embodiment.

In the above-described clamp circuit 94 according to the fifth embodiment, the two diodes 94B and 94C are arranged with their cathodes connected to each other. However, the present invention is not limited to such an arrangement. For example, as in a clamp circuit 111 according to a seventh embodiment illustrated in FIG. 21, two diodes 111B and 111C connected to a ground 111A may be arranged with their anodes connected to each other. Alternatively, a set of the diodes 94B and 94C or the diodes 111B and 111C oppositely faced to each other may be connected plural in series. Those arrangements of the diodes 94B and 94C according to the fifth embodiment and the diodes 111B and 111C according to the seventh embodiment can also be applied to the diodes 105B and 106B (high-impedance elements) of the clamp circuits 105 and 106 according to the sixth embodiment.

Figure 22:
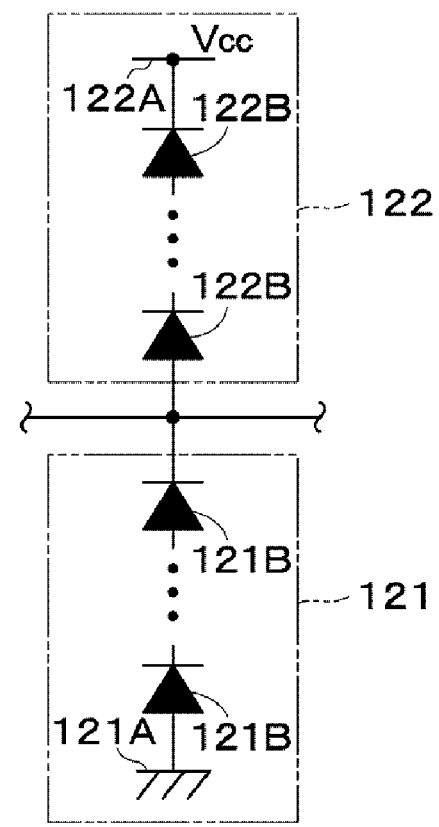
FIG. 22 is a circuit diagram illustrating a clamp circuit in an eighth embodiment.

In the above-described clamp circuits 105 and 106 according to the sixth embodiment, the high-impedance element is constituted by the single diode 105B or 106B. However, the present invention is not limited to such a configuration. For example, as in clamp circuits 121 and 122 according to an eighth embodiment illustrated in FIG. 22, plural diodes 121B and plural diodes 122B may be connected in series to a ground 121A and a drive voltage source 122A, respectively, in such a way that forward directions of those diodes are oriented in the same direction. In that case, respective adjacent two of the diodes 121B and the diodes 122B are interconnected with a cathode of one and an anode of the other connected to each other. Such an arrangement can reduce reverse currents flowing through the diodes 121B and the diodes 122B, and can easily increase the resistance values of the clamp circuits 121 and 122.

In the fifth to eighth embodiments, the diodes 94B, 94C, 105B, 106B, 111B, 111C, 121B and 122B are employed as the high-impedance elements. Instead of the diodes 94B, 94C, 105B, 106B, 111B, 111C, 121B and 122B, however, bipolar transistors may be employed, for example, in the form that a base and a collector of each bipolar transistor are short-circuited so as to utilize a base-emitter characteristic. Alternatively, a gate and a source of a field effect transistor may be short-circuited so as to utilize a gate-source characteristic.

As another example, a high-resistance element, a high-resistance semiconductor film, or the like may also be used as the high-impedance element. The high-resistance semiconductor film can be formed by any of such processes as sputtering, CVD, MBE, and vacuum deposition, but some other suitable film forming method may be used instead. One example of the high-resistance semiconductor film is an oxide semiconductor film, but another type of high-resistance semiconductor film can also be used. Further, the high-impedance element may be obtained by forming an insulator substrate made of, e.g., silicon, gallium or arsenic, and by reducing the resistance of the substrate. The resistance of the substrate can be reduced, for example, by adding impurities to the substrate with, e.g., thermal diffusion or ion implanting.

In the above-described sixth embodiment, the same first and second clamp circuits 105 and 106 (i.e., the same clamp circuit unit 104) are connected to each of the transparent electrodes 10 and 11. However, the present invention is not limited to such an arrangement. For example, different clamp circuit units may be connected to the two transparent electrodes, respectively. In that case, a first DC constant-voltage source of a first clamp circuit connected to one of the transparent electrodes and a first DC constant-voltage source of a first clamp circuit connected to the other transparent electrode may have different potentials from each other. Similarly, a second DC constant-voltage source of a second clamp circuit connected to one of the transparent electrodes and a second DC constant-voltage source of a second clamp circuit connected to the other transparent electrode may have different potentials from each other. Further, respective resistance values R0 of the diodes 105B and 106B in the clamp circuits 105 and 106 may differ from each other.

While, in the fifth and sixth embodiments, the filter units 93 and 103 for removing the radiation noises are constituted as active filters including operational amplifiers 93C and 103C each having the high input impedance, the filter units may be each constituted as a passive filter not including the operational amplifier.

In the above-described fifth or sixth embodiment, the clamp circuit 94 or the clamp circuits 105 and 106 are connected to each of the transparent electrodes 10 and 11 employed in the first embodiment. However, the present invention is not limited to such an arrangement. For example, the clamp circuit 94 or the clamp circuits 105 and 106 may be connected to the electrodes 46, 47, 67, 68, 86 and 87 employed in the second to fourth embodiments.

In the above-described embodiments, the electrodes 10, 11, 46, 47, etc. for detecting the biological signals (electrocardiographic signal) are disposed on, e.g., the upper surfaces of the display windows 5, 43, 63 and 83, or on the upper surfaces of the operating buttons 45, 65, 66 and 85, which are attached to the housings 2, 42, 62 and 82 of the electrocardiographic signal detection devices 1, 41, 61, 81, 91 and 101. However, the present invention is not limited to those cases. For example, the present invention can also be applied to an electrocardiographic signal detection device provided with a plurality of detection probes each including a cord, an electrode disposed at a distal end of the cord, and an insulating film disposed on the electrode (on a tip surface of the electrode) and having one surface, which is positioned oppositely away from the other surface being in contact with the electrode and which serves as a contact surface to be contacted with the living body.

The invention claimed is:

1. An electrocardiographic signal detection device comprising:
   at least one pair of electrodes that detect electrical signals of a living body;
   an insulating film disposed on the at least one pair of electrodes, the insulating film having a living body contact surface;
   a differential amplifier that generates an electrocardiographic signal by differentially amplifying the electrical signals of the living body; and
   an arithmetic processing unit that obtains biological information based on the electrocardiographic signal generated by the differential amplifier,
   wherein the insulating film and the at least one pair of electrodes are arranged such that the electrical signals of the living body are detected through capacitive coupling between the living body in contact with the living body contact surface of the insulating film and the at least one pair of electrodes.

2. The electrocardiographic signal detection device according to claim 1, further comprising a respective filter unit connected to each of the at least one pair of electrodes, the filter units configured to reduce noise in the detected electrical signals of a living body.

3. The electrocardiographic signal detection device according to claim 2, wherein the filer unit comprises a low pass filer.

4. The electrocardiographic signal detection device according to claim 2, further comprising a baseline variation suppression unit disposed between the respective filter units and the differential amplifier, the baseline variation suppression unit operable to suppress variations in a baseline of signals output from the respective filter units.

5. The electrocardiographic signal detection device according to claim 1, wherein the at least one pair of electrodes are connected to input terminals of the differential amplifier, the electrocardiographic signal detection device further comprising:
   at least one clamp circuit connected to the input terminal of the differential amplifier, the at least one clamp circuit including at least one high-impedance element, and
   the at least one clamp circuit configured such that a potential at a connected end of the clamp circuit is held constant, and an impedance of the differential amplifier from the connected end of the clamp circuit is larger than an impedance of the clamp circuit.

6. An electrocardiographic signal detection device comprising:
   a housing having a display window;
   at least one pair of transparent electroconductive electrodes disposed on a surface of the display window that detect electrical signals of a living body;
   a transparent insulating film disposed on the at least one pair of electrodes, the insulating film having a living body contact surface;
   a differential amplifier that generates an electrocardiographic signal by differentially amplifying the electrical signals of the living body;
   an arithmetic processing unit that obtains biological information based on the electrocardiographic signal generated by the differential amplifier;
   a display panel disposed in the housing and configured to display information through the display window, the at least one pair of transparent electroconductive electrodes, and through the transparent insulating film; and
   an information display circuit operable to display the display information on the display panel,
   wherein the transparent insulating film and the at least one pair of transparent electroconductive electrodes are arranged such that the electrical signals of the living body are detected through capacitive coupling between the living body in contact with the living body contact surface of the transparent insulating film and the at least one pair of transparent electroconductive electrodes.

7. The electrocardiographic signal detection device according to claim 6, wherein the transparent insulating film covers substantially an entire surface of the display window.

8. The electrocardiographic signal detection device according to claim 6, further comprising a touch panel disposed at an underside of the display window and adapted for entering input information through the display window, a drive circuit for driving the touch panel, and a control unit for controlling the arithmetic processing unit in accordance with the input information entered through the touch panel.

9. The electrocardiographic signal detection device according to claim 6, further comprising a respective filter unit connected to each of the at least one pair of electrodes, the filter units configured to reduce noise in the detected electrical signals of a living body.

10. The electrocardiographic signal detection device according to claim 9, wherein the filer unit comprises a low pass filer.

11. The electrocardiographic signal detection device according to claim 9, further comprising a baseline variation suppression unit disposed between the respective filter units and the differential amplifier, the baseline variation suppression unit operable to suppress variations in a baseline of signals output from the respective filter units.

12. The electrocardiographic signal detection device according to claim 6, wherein the at least one pair of electrodes are connected to input terminals of the differential amplifier, the electrocardiographic signal detection device further comprising:
   at least one clamp circuit connected to the input terminal of the differential amplifier, the at least one clamp circuit including at least one high-impedance element, and
   the at least one clamp circuit configured such that a potential at a connected end of the clamp circuit is held constant, and an impedance of the differential amplifier from the connected end of the clamp circuit is larger than an impedance of the clamp circuit.

13. An electrocardiographic signal detection device comprising:
   a housing having a display window;
   an operating button disposed on the housing;
   a first electroconductive electrode disposed on the operating button that detects an electrical signal of a living body;
   a first insulating film disposed on the first electroconductive electrode and having a first living body contact surface;
   at least one second transparent electroconductive electrode disposed on a surface of the display window that detects an electrical signal of the living body;
   a second transparent insulating film disposed on the at least one second transparent electroconductive electrode and having a second living body contact surface;
   a differential amplifier that generates an electrocardiographic signal by differentially amplifying a first electrical signal of the living body detected through capacitive coupling between the living body in contact with the second living body contact surface of the second transparent insulating film and the at least one second transparent electroconductive electrode, and a second electrical signal of the living body detected through capacitive coupling between the living body in contact with the first living body contact surface of the first insulating film and the first electroconductive electrode;

an arithmetic processing unit that obtains biological information based on the electrocardiographic signal generated by the differential amplifier;

a display panel disposed in the housing and configured to display information through the display window, the at least one second transparent electroconductive electrode, and through the second transparent insulating film; and an information display circuit operable to display the display information on the display panel.

14. The electrocardiographic signal detection device according to claim 13, wherein the second transparent insulating film covers substantially an entire surface of the display window.

15. The electrocardiographic signal detection device according to claim 13, further comprising:

a touch panel disposed adjacent the display window and configured to accept input information through the display window;

a drive circuit that drives the touch panel; and a control unit that controls the arithmetic processing unit in accordance with the input information.

16. The electrocardiographic signal detection device according to claim 13, wherein the at least one pair of electrodes are connected to input terminals of the differential amplifier, the electrocardiographic signal detection device further comprising:

at least one clamp circuit connected to the input terminal of the differential amplifier, the at least one clamp circuit including at least one high-impedance element, and the at least one clamp circuit configured such that a potential at a connected end of the clamp circuit is held constant, and an impedance of the differential amplifier from the connected end of the clamp circuit is larger than an impedance of the clamp circuit.

17. The electrocardiographic signal detection device according to claim 13, further comprising a respective filter unit connected to each of the at least one pair of electrodes, the filter units configured to reduce noise in the detected electrical signals of a living body.

18. The electrocardiographic signal detection device according to claim 17, wherein the filer unit comprises a low pass filer.

19. The electrocardiographic signal detection device according to claim 17, further comprising a baseline variation suppression unit disposed between the respective filter units and the differential amplifier, the baseline variation suppression unit operable to suppress variations in a baseline of signals output from the respective filter units.

* * * * *